United States Patent
Groll

(10) Patent No.: US 7,718,439 B2
(45) Date of Patent: *May 18, 2010

(54) SYSTEM AND METHOD FOR CODING INFORMATION ON A BIOSENSOR TEST STRIP

(75) Inventor: Henning Groll, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 963 days.

This patent is subject to a terminal disclaimer.

(21) Appl. No.: 10/872,007

(22) Filed: Jun. 18, 2004

(65) Prior Publication Data

US 2005/0019953 A1    Jan. 27, 2005

Related U.S. Application Data

(60) Provisional application No. 60/480,199, filed on Jun. 20, 2003.

(51) Int. Cl.
*G01N 21/00* (2006.01)
*G01N 25/18* (2006.01)
*G01N 27/00* (2006.01)
*G01N 33/48* (2006.01)
*C12M 1/00* (2006.01)

(52) U.S. Cl. .................. 436/149; 436/63; 422/58; 422/82.01; 204/403.01; 204/403.14

(58) Field of Classification Search .................. 435/58; 436/149, 63; 422/58, 82.01; 204/403.01, 204/403.14
See application file for complete search history.

(56) References Cited

U.S. PATENT DOCUMENTS

| | | | |
|---|---|---|---|
| 3,526,480 A | 9/1970 | Findl et al. | |
| 3,551,295 A | 12/1970 | Dyer | |
| 3,621,381 A | 11/1971 | Eckfeldt | |
| 3,715,192 A | 2/1973 | Wenz et al. | |
| 3,720,093 A | 3/1973 | Gill | |
| 3,763,422 A | 10/1973 | MacPhee et al. | |
| 3,770,607 A | 11/1973 | Williams | |
| 3,776,832 A | 12/1973 | Oswin et al. | |
| 3,838,033 A | 9/1974 | Mindt et al. | |

(Continued)

FOREIGN PATENT DOCUMENTS

| | | |
|---|---|---|
| AU | 737 787 | 8/2001 |
| DE | 36 43 263 A | 7/1988 |
| DE | 40 11 428 A1 | 11/1990 |
| DE | 298 14 997 U1 | 8/1993 |
| DE | 199 36 693 A | 2/2001 |

(Continued)

OTHER PUBLICATIONS

Skladal, "Compensation of Temperature Variations Disturbing Performance of an Amperometric Biosensor for Continuous Monitoring," Sensors and Actuators B, Elsevier Sequoia S.A., Lausanne, CH, vol. 28, No. 1, Jul. 1, 1995, pp. 59-62, XP004004390, ISSN: 0925-4005.

(Continued)

*Primary Examiner*—Lore Jarrett
(74) *Attorney, Agent, or Firm*—Woodard, Emhardt, Moriarty, McNett & Henry LLP

(57) ABSTRACT

The present invention provides a test strip for measuring a concentration of an analyte of interest in a biological fluid, wherein the test strip may be encoded with information that can be read by a test meter into which the test strip is inserted.

3 Claims, 13 Drawing Sheets

U.S. PATENT DOCUMENTS

| | | |
|---|---|---|
| 3,902,970 A | 9/1975 | Levin |
| 3,919,627 A | 11/1975 | Allen |
| 3,925,183 A | 12/1975 | Oswin et al. |
| 3,937,615 A | 2/1976 | Clack et al. |
| 3,980,437 A | 9/1976 | Kishimoto et al. |
| 4,005,002 A | 1/1977 | Racine et al. |
| 4,008,448 A | 2/1977 | Muggli |
| 4,040,908 A | 8/1977 | Clark, Jr. |
| 4,053,381 A | 10/1977 | Hamblen et al. |
| 4,065,263 A | 12/1977 | Woodbridge, III |
| 4,086,631 A | 4/1978 | Vick |
| 4,123,701 A | 10/1978 | Josefsen et al. |
| 4,127,448 A | 11/1978 | Schick et al. |
| 4,184,936 A | 1/1980 | Paul et al. |
| 4,214,968 A | 7/1980 | Battaglia et al. |
| 4,217,196 A | 8/1980 | Huch |
| 4,224,125 A | 9/1980 | Nakamura et al. |
| 4,225,410 A | 9/1980 | Pace |
| 4,230,537 A | 10/1980 | Delente et al. |
| 4,233,029 A | 11/1980 | Columbus |
| 4,260,680 A | 4/1981 | Muramatsu et al. |
| 4,263,343 A | 4/1981 | Kim |
| 4,265,250 A | 5/1981 | Parker |
| 4,273,134 A | 6/1981 | Ricciardelli |
| 4,273,639 A | 6/1981 | Gottermeier |
| 4,297,569 A | 10/1981 | Flies |
| 4,301,412 A | 11/1981 | Hill et al. |
| 4,303,887 A | 12/1981 | Hill et al. |
| 4,323,536 A | 4/1982 | Columbus |
| 4,329,642 A | 5/1982 | Luthi et al. |
| 4,366,033 A | 12/1982 | Richter et al. |
| 4,407,290 A | 10/1983 | Wilber |
| 4,407,959 A | 10/1983 | Tsuji et al. |
| 4,413,407 A | 11/1983 | Columbus |
| 4,413,628 A | 11/1983 | Tamulis |
| 4,420,564 A | 12/1983 | Tsuji et al. |
| 4,431,004 A | 2/1984 | Bessman et al. |
| 4,436,094 A | 3/1984 | Cerami |
| 4,440,175 A | 4/1984 | Wilkins |
| 4,476,149 A | 10/1984 | Poppe et al. |
| 4,477,314 A | 10/1984 | Richter et al. |
| 4,477,575 A | 10/1984 | Vogel et al. |
| 4,499,423 A | 2/1985 | Matthiessen |
| 4,510,383 A | 4/1985 | Ruppender |
| 4,517,291 A | 5/1985 | Seago |
| 4,545,382 A | 10/1985 | Higgins et al. |
| 4,547,735 A | 10/1985 | Kiesewetter et al. |
| 4,552,458 A | 11/1985 | Lowne |
| 4,571,292 A | 2/1986 | Liu et al. |
| 4,578,716 A | 3/1986 | van Rijckevorsel et al. |
| 4,592,893 A | 6/1986 | Poppe et al. |
| 4,628,193 A | 12/1986 | Blum |
| 4,642,295 A | 2/1987 | Baker |
| 4,648,665 A | 3/1987 | Davis et al. |
| 4,652,830 A | 3/1987 | Brown |
| 4,654,197 A | 3/1987 | Lilja et al. |
| 4,671,288 A | 6/1987 | Gough |
| 4,676,653 A | 6/1987 | Strohmeier et al. |
| 4,679,562 A | 7/1987 | Luksha |
| 4,682,602 A | 7/1987 | Prohaska |
| 4,686,479 A | 8/1987 | Young et al. |
| 4,703,017 A | 10/1987 | Campbell et al. |
| 4,703,756 A | 11/1987 | Gough et al. |
| 4,711,245 A | 12/1987 | Higgins et al. |
| 4,713,347 A | 12/1987 | Mitchell et al. |
| 4,714,874 A | 12/1987 | Morris et al. |
| 4,731,726 A | 3/1988 | Allen, III |
| 4,734,184 A | 3/1988 | Burleigh et al. |
| 4,750,496 A | 6/1988 | Reinhart et al. |
| 4,759,828 A | 7/1988 | Young et al. |
| 4,789,804 A | 12/1988 | Karube et al. |
| 4,795,542 A | 1/1989 | Ross et al. |
| 4,797,256 A | 1/1989 | Watlington, IV |
| 4,805,624 A | 2/1989 | Yao et al. |
| 4,806,311 A | 2/1989 | Greenquist |
| 4,806,312 A | 2/1989 | Greenquist |
| 4,810,203 A | 3/1989 | Komatsu |
| 4,816,224 A | 3/1989 | Vogel et al. |
| 4,820,399 A | 4/1989 | Senda et al. |
| 4,820,636 A | 4/1989 | Hill et al. |
| 4,832,814 A | 5/1989 | Root |
| 4,834,234 A | 5/1989 | Sacherer et al. |
| 4,849,330 A | 7/1989 | Humphries et al. |
| 4,865,873 A | 9/1989 | Cole, Jr. et al. |
| 4,877,580 A | 10/1989 | Aronowitz et al. |
| 4,897,162 A | 1/1990 | Lewandowski et al. |
| 4,897,173 A | 1/1990 | Nankai et al. |
| 4,919,770 A | 4/1990 | Preidel et al. |
| 4,927,516 A | 5/1990 | Yamaguchi et al. |
| 4,935,105 A | 6/1990 | Churchouse |
| 4,935,106 A | 6/1990 | Liston et al. |
| 4,935,346 A | 6/1990 | Phillips et al. |
| 4,938,860 A | 7/1990 | Wogoman |
| 4,940,945 A | 7/1990 | Littlejohn et al. |
| 4,954,087 A | 9/1990 | Lauks et al. |
| 4,956,275 A | 9/1990 | Zuk et al. |
| 4,963,814 A | 10/1990 | Parks |
| 4,970,145 A | 11/1990 | Bennetto et al. |
| 4,975,647 A | 12/1990 | Downer et al. |
| 4,976,724 A | 12/1990 | Nieto et al. |
| 4,999,582 A | 3/1991 | Parks et al. |
| 4,999,632 A | 3/1991 | Parks |
| 5,018,164 A | 5/1991 | Brewer et al. |
| 5,019,974 A | 5/1991 | Beckers |
| 5,035,862 A | 7/1991 | Dietze et al. |
| 5,039,618 A | 8/1991 | Stone |
| 5,049,487 A | 9/1991 | Phillips et al. |
| 5,053,199 A | 10/1991 | Keiser et al. |
| 5,059,394 A | 10/1991 | Phillips et al. |
| 5,066,372 A | 11/1991 | Weetall |
| 5,075,077 A | 12/1991 | Durley, III et al. |
| 5,096,669 A | 3/1992 | Lauks et al. |
| 5,108,564 A | 4/1992 | Szuminsky et al. |
| 5,112,455 A | 5/1992 | Cozzette et al. |
| 5,112,758 A | 5/1992 | Fellman et al. |
| 5,118,183 A | 6/1992 | Cargill et al. |
| 5,120,420 A | 6/1992 | Nankai et al. |
| 5,122,244 A | 6/1992 | Hoenes et al. |
| 5,126,952 A | 6/1992 | Kildal-Brandt et al. |
| 5,128,015 A | 7/1992 | Szuminsky et al. |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |
| 5,179,288 A | 1/1993 | Miffitt et al. |
| 5,182,707 A | 1/1993 | Cooper et al. |
| 5,187,100 A | 2/1993 | Matzinger et al. |
| 5,192,415 A | 3/1993 | Yoshioka et al. |
| 5,220,920 A | 6/1993 | Gharib |
| 5,232,516 A | 8/1993 | Hed |
| 5,232,668 A | 8/1993 | Grant et al. |
| 5,234,813 A | 8/1993 | McGeehan et al. |
| 5,243,516 A | 9/1993 | White |
| 5,246,858 A | 9/1993 | Arbuckle et al. |
| 5,250,439 A | 10/1993 | Musho et al. |
| 5,264,103 A | 11/1993 | Yoshioka et al. |
| 5,266,179 A | 11/1993 | Nankai et al. |
| 5,269,891 A | 12/1993 | Colin |
| 5,279,294 A | 1/1994 | Anderson et al. |
| 5,281,395 A | 1/1994 | Markart et al. |
| 5,284,770 A | 2/1994 | Adrian et al. |
| 5,286,362 A | 2/1994 | Hoenes et al. |
| 5,288,636 A | 2/1994 | Pollmann et al. |
| 5,296,192 A | 3/1994 | Carroll et al. |

| | | | | | |
|---|---|---|---|---|---|
| 5,304,468 A | 4/1994 | Phillips et al. | 5,639,671 A | 6/1997 | Bogart et al. |
| 5,306,623 A | 4/1994 | Kiser | 5,642,734 A | 7/1997 | Ruben et al. |
| 5,311,426 A | 5/1994 | Donohue et al. | 5,645,798 A | 7/1997 | Schreiber et al. |
| 5,312,762 A | 5/1994 | Guiseppi-Elie | 5,650,061 A | 7/1997 | Kuhr et al. |
| 5,344,754 A | 9/1994 | Zweig | 5,650,062 A | 7/1997 | Ikeda et al. |
| 5,352,351 A | 10/1994 | White et al. | 5,653,863 A | 8/1997 | Genshaw et al. |
| 5,353,351 A | 10/1994 | Bartoli et al. | 5,654,178 A | 8/1997 | Fitzpatrick et al. |
| 5,366,609 A | 11/1994 | White et al. | 5,656,142 A | 8/1997 | Park et al. |
| 5,371,687 A | 12/1994 | Holmes, II et al. | 5,656,502 A | 8/1997 | MacKay et al. |
| 5,376,254 A | 12/1994 | Fisher | 5,658,443 A | 8/1997 | Yamamoto et al. |
| 5,379,214 A | 1/1995 | Arbuckle et al. | 5,658,802 A | 8/1997 | Hayes et al. |
| 5,384,028 A * | 1/1995 | Ito ............................. 257/253 | 5,665,215 A | 9/1997 | Bussmann et al. |
| 5,385,846 A | 1/1995 | Kuhn et al. | 5,670,031 A | 9/1997 | Hintsche et al. |
| 5,389,215 A | 2/1995 | Horiuchi et al. | 5,682,884 A | 11/1997 | Hill et al. |
| 5,395,504 A | 3/1995 | Saurer et al. | 5,686,659 A | 11/1997 | Neel et al. |
| 5,405,511 A | 4/1995 | Brown et al. | 5,691,486 A | 11/1997 | Behringer et al. |
| 5,411,647 A | 5/1995 | Johnson et al. | 5,691,633 A | 11/1997 | Liu et al. |
| 5,413,690 A * | 5/1995 | Kost et al. ................ 205/777.5 | 5,695,623 A | 12/1997 | Michel et al. |
| 5,413,764 A | 5/1995 | Haar | 5,698,083 A | 12/1997 | Glass |
| 5,418,142 A | 5/1995 | Kiser et al. | 5,700,695 A | 12/1997 | Yassinzadeh et al. |
| 5,421,189 A | 6/1995 | Dussault | 5,708,247 A | 1/1998 | McAleer et al. |
| 5,424,035 A | 6/1995 | Hones et al. | 5,710,622 A | 1/1998 | Neel et al. |
| 5,426,032 A | 6/1995 | Phillips et al. | 5,719,667 A | 2/1998 | Miers |
| 5,437,772 A | 8/1995 | De Castro et al. | 5,720,862 A | 2/1998 | Hamamoto et al. |
| 5,437,999 A | 8/1995 | Diebold et al. | 5,723,284 A | 3/1998 | Ye |
| 5,438,271 A | 8/1995 | White et al. | 5,727,548 A | 3/1998 | Hill et al. |
| 5,439,826 A | 8/1995 | Kontorovich | 5,728,074 A | 3/1998 | Castellano et al. |
| 5,445,967 A | 8/1995 | Deuter | 5,745,308 A | 4/1998 | Spangenberg |
| 5,447,837 A | 9/1995 | Urnovitz | 5,757,666 A | 5/1998 | Schreiber et al. |
| 5,453,360 A | 9/1995 | Yu | 5,759,794 A | 6/1998 | Levine et al. |
| 5,469,846 A | 11/1995 | Khan | 5,762,770 A | 6/1998 | Pritchard et al. |
| 5,470,533 A | 11/1995 | Shindo et al. | 5,776,710 A | 7/1998 | Levine et al. |
| 5,477,326 A | 12/1995 | Dosmann | 5,780,304 A | 7/1998 | Matzinger et al. |
| 5,489,414 A | 2/1996 | Schreiber et al. | 5,786,584 A | 7/1998 | Button et al. |
| 5,494,638 A | 2/1996 | Gullick | 5,788,833 A | 8/1998 | Lewis et al. |
| 5,500,350 A | 3/1996 | Baker et al. | 5,789,255 A | 8/1998 | Yu |
| 5,504,011 A | 4/1996 | Gavin et al. | 5,792,668 A | 8/1998 | Fuller et al. |
| 5,508,171 A | 4/1996 | Walling et al. | 5,798,031 A | 8/1998 | Charlton et al. |
| 5,508,200 A | 4/1996 | Tiffany et al. | 5,801,057 A | 9/1998 | Smart et al. |
| 5,508,203 A | 4/1996 | Fuller et al. | 5,820,551 A | 10/1998 | Hill et al. |
| 5,509,410 A | 4/1996 | Hill et al. | 5,820,622 A | 10/1998 | Gross et al. |
| 5,515,170 A | 5/1996 | Matzinger | 5,832,921 A | 11/1998 | Lennert et al. |
| 5,515,847 A | 5/1996 | Braig et al. | 5,834,217 A | 11/1998 | Levine et al. |
| 5,526,111 A | 6/1996 | Collins et al. | 5,837,546 A | 11/1998 | Allen et al. |
| 5,526,120 A | 6/1996 | Jina et al. | 5,843,691 A | 12/1998 | Douglas et al. |
| 5,526,808 A | 6/1996 | Kaminsky | 5,843,692 A | 12/1998 | Phillips et al. |
| 5,532,128 A | 7/1996 | Eggers et al. | 5,846,744 A | 12/1998 | Athey et al. |
| 5,552,116 A | 9/1996 | Yokota et al. | 5,849,174 A | 12/1998 | Sanghera et al. |
| 5,554,531 A | 9/1996 | Zweig | 5,856,195 A | 1/1999 | Charlton et al. |
| 5,556,789 A | 9/1996 | Goerlach-Graw et al. | 5,873,990 A | 2/1999 | Wojciechowski et al. |
| 5,563,031 A | 10/1996 | Yu | 5,883,378 A | 3/1999 | Irish et al. |
| 5,563,042 A | 10/1996 | Phillips et al. | 5,885,839 A | 3/1999 | Lingane et al. |
| 5,569,591 A | 10/1996 | Kell et al. | 5,890,489 A | 4/1999 | Elden |
| 5,569,608 A | 10/1996 | Sommer | 5,904,898 A | 5/1999 | Markart |
| 5,572,159 A | 11/1996 | McFarland | 5,911,872 A | 6/1999 | Lewis et al. |
| 5,575,895 A | 11/1996 | Ikeda et al. | 5,916,156 A | 6/1999 | Hildenbrand et al. |
| 5,576,073 A | 11/1996 | Kickelhain | 5,921,925 A | 7/1999 | Cartmell et al. |
| 5,580,794 A | 12/1996 | Allen | 5,922,530 A | 7/1999 | Yu |
| 5,582,697 A | 12/1996 | Ikeda et al. | 5,922,591 A | 7/1999 | Anderson et al. |
| 5,593,390 A | 1/1997 | Castellano et al. | 5,925,021 A | 7/1999 | Castellano et al. |
| 5,593,739 A | 1/1997 | Kickelhain | 5,945,341 A | 8/1999 | Howard, III |
| 5,594,906 A | 1/1997 | Holmes, II et al. | 5,948,289 A | 9/1999 | Noda et al. |
| 5,597,532 A | 1/1997 | Connolly | 5,951,836 A | 9/1999 | McAleer et al. |
| 5,604,110 A | 2/1997 | Baker et al. | 5,965,380 A | 10/1999 | Heller |
| 5,605,662 A | 2/1997 | Heller et al. | 5,968,760 A | 10/1999 | Phillips et al. |
| 5,605,837 A | 2/1997 | Karimi et al. | 5,971,923 A | 10/1999 | Finger |
| 5,611,900 A | 3/1997 | Worden et al. | 5,989,917 A | 11/1999 | McAleer et al. |
| 5,620,579 A | 4/1997 | Genshaw et al. | 5,997,817 A | 12/1999 | Crismore et al. |
| 5,620,863 A | 4/1997 | Tomasco et al. | 6,004,441 A | 12/1999 | Fujiwara et al. |
| 5,628,890 A | 5/1997 | Carter et al. | 6,013,170 A | 1/2000 | Meade |
| 5,630,986 A | 5/1997 | Charlton et al. | 6,042,714 A | 3/2000 | Lin et al. |
| 5,635,362 A | 6/1997 | Levine et al. | 6,044,285 A | 3/2000 | Chaiken et al. |
| 5,635,364 A | 6/1997 | Clark et al. | 6,045,567 A | 4/2000 | Taylor et al. |

| | | | | | | |
|---|---|---|---|---|---|---|
| 6,061,128 | A | 5/2000 | Zweig et al. | 6,316,264 | B1 | 11/2001 | Corey et al. |
| 6,071,391 | A | 6/2000 | Gotoh et al. | 6,325,917 | B1 | 12/2001 | Maxwell et al. |
| 6,087,182 | A | 7/2000 | Jeng et al. | 6,326,160 | B1 | 12/2001 | Dunn et al. |
| 6,091,975 | A | 7/2000 | Daddona et al. | 6,329,161 | B1 | 12/2001 | Heller et al. |
| 6,102,872 | A | 8/2000 | Doneen et al. | 6,330,464 | B1 | 12/2001 | Colvin, Jr. et al. |
| 6,103,033 | A | 8/2000 | Say et al. | 6,335,203 | B1 | 1/2002 | Patel et al. |
| 6,120,676 | A | 9/2000 | Heller et al. | 6,338,790 | B1 | 1/2002 | Feldman et al. |
| 6,121,009 | A | 9/2000 | Heller et al. | 6,340,428 | B1 | 1/2002 | Ikeda et al. |
| 6,121,050 | A | 9/2000 | Han | 6,342,364 | B1 | 1/2002 | Watanabe et al. |
| 6,126,609 | A | 10/2000 | Keith et al. | 6,349,230 | B1 | 2/2002 | Kawanaka |
| 6,128,519 | A | 10/2000 | Say | 6,358,752 | B1 | 3/2002 | Durst et al. |
| 6,129,823 | A | 10/2000 | Hughes et al. | 6,377,894 | B1 | 4/2002 | Deweese et al. |
| 6,134,461 | A | 10/2000 | Say et al. | 6,377,896 | B1 | 4/2002 | Sato et al. |
| 6,136,549 | A | 10/2000 | Feistel | 6,379,513 | B1 | 4/2002 | Chambers et al. |
| 6,136,610 | A | 10/2000 | Polito et al. | 6,389,891 | B1 | 5/2002 | D'Angelico et al. |
| 6,143,164 | A | 11/2000 | Heller et al. | 6,391,558 | B1 | 5/2002 | Henkens et al. |
| 6,143,247 | A | 11/2000 | Sheppard, Jr. et al. | 6,391,645 | B1 | 5/2002 | Huang et al. |
| 6,144,869 | A | 11/2000 | Berner et al. | 6,394,952 | B1 | 5/2002 | Anderson et al. |
| 6,150,124 | A | 11/2000 | Riedel | 6,395,227 | B1 | 5/2002 | Kiser et al. |
| 6,153,069 | A | 11/2000 | Pottgen et al. | 6,399,258 | B2 | 6/2002 | O'Brien et al. |
| RE36,991 | E | 12/2000 | Yamamoto et al. | 6,401,532 | B2 | 6/2002 | Lubbers |
| 6,156,051 | A | 12/2000 | Schraga | 6,413,213 | B1 | 7/2002 | Essenpreis et al. |
| 6,156,173 | A | 12/2000 | Gotoh et al. | 6,413,395 | B1 | 7/2002 | Bhullar et al. |
| 6,159,745 | A | 12/2000 | Roberts et al. | 6,413,410 | B1 | 7/2002 | Hodges et al. |
| 6,162,611 | A | 12/2000 | Heller et al. | 6,420,128 | B1 | 7/2002 | Ouyang et al. |
| 6,162,639 | A | 12/2000 | Douglas | 6,444,115 | B1 | 9/2002 | Hodges et al. |
| 6,168,563 | B1 | 1/2001 | Brown | 6,447,657 | B1 | 9/2002 | Bhullar et al. |
| 6,168,957 | B1 | 1/2001 | Matzinger et al. | 6,447,659 | B1 | 9/2002 | Peng |
| 6,170,318 | B1 | 1/2001 | Lewis | 6,454,921 | B1 | 9/2002 | Hodges et al. |
| 6,174,420 | B1 | 1/2001 | Hodges et al. | 6,461,496 | B1 | 10/2002 | Feldman et al. |
| 6,175,752 | B1 | 1/2001 | Say et al. | 6,475,360 | B1 | 11/2002 | Hodges et al. |
| 6,176,988 | B1 | 1/2001 | Kessler | 6,475,372 | B1 | 11/2002 | Ohara et al. |
| 6,179,979 | B1 | 1/2001 | Hodges et al. | 6,484,046 | B1 | 11/2002 | Say et al. |
| 6,180,062 | B1 | 1/2001 | Naka et al. | 6,485,923 | B1 | 11/2002 | Yani et al. |
| 6,180,416 | B1 | 1/2001 | Kurnik et al. | 6,488,827 | B1 | 12/2002 | Shartle |
| 6,193,873 | B1 | 2/2001 | Ohara et al. | 6,489,133 | B2 | 12/2002 | Phillips et al. |
| 6,197,040 | B1 | 3/2001 | LeVaughn et al. | 6,491,803 | B1 | 12/2002 | Shen et al. |
| 6,200,773 | B1 | 3/2001 | Ouyang et al. | 6,491,870 | B2 | 12/2002 | Patel et al. |
| 6,201,607 | B1 | 3/2001 | Roth et al. | 6,501,976 | B1 | 12/2002 | Sohrab |
| 6,203,952 | B1 | 3/2001 | O'Brien et al. | 6,503,381 | B1 | 1/2003 | Gotoh et al. |
| 6,206,282 | B1 | 3/2001 | Hayes, Sr. et al. | 6,512,986 | B1 | 1/2003 | Harmon |
| 6,206,292 | B1 | 3/2001 | Robertz et al. | 6,514,718 | B2 | 2/2003 | Heller et al. |
| 6,218,571 | B1 | 4/2001 | Zheng et al. | 6,514,769 | B2 | 2/2003 | Lee |
| 6,225,078 | B1 | 5/2001 | Ikeda et al. | 6,521,110 | B1 | 2/2003 | Hodges et al. |
| 6,226,081 | B1 | 5/2001 | Fantone et al. | 6,521,182 | B1 | 2/2003 | Shartle et al. |
| 6,241,862 | B1 | 6/2001 | McAleer et al. | 6,525,330 | B2 | 2/2003 | Paolini et al. |
| 6,246,330 | B1 | 6/2001 | Nielsen | 6,525,549 | B1 | 2/2003 | Poellmann |
| 6,246,966 | B1 | 6/2001 | Perry | 6,526,298 | B1 | 2/2003 | Khalil et al. |
| 6,251,260 | B1 | 6/2001 | Heller et al. | 6,531,239 | B2 | 3/2003 | Heller |
| 6,258,229 | B1 | 7/2001 | Winarta et al. | 6,531,322 | B1 | 3/2003 | Jurik et al. |
| 6,258,254 | B1 | 7/2001 | Miyamoto et al. | 6,538,735 | B1 | 3/2003 | Duebendorfer et al. |
| 6,259,937 | B1 | 7/2001 | Schulman et al. | 6,540,890 | B1 | 4/2003 | Bhullar et al. |
| 6,261,519 | B1 | 7/2001 | Harding et al. | 6,540,891 | B1 | 4/2003 | Stewart et al. |
| 6,262,749 | B1 | 7/2001 | Finger et al. | 6,541,266 | B2 | 4/2003 | Modzelewski et al. |
| 6,268,162 | B1 | 7/2001 | Phillips et al. | 6,544,474 | B2 | 4/2003 | Douglas |
| 6,270,637 | B1 | 8/2001 | Crismore et al. | 6,549,796 | B2 | 4/2003 | Sohrab |
| 6,271,044 | B1 | 8/2001 | Ballerstadt et al. | 6,551,494 | B1 | 4/2003 | Heller et al. |
| 6,272,364 | B1 | 8/2001 | Kurnik | 6,555,061 | B1 | 4/2003 | Leong et al. |
| 6,277,641 | B1 | 8/2001 | Yager | 6,558,528 | B1 | 5/2003 | Matzinger |
| 6,281,006 | B1 | 8/2001 | Heller et al. | 6,560,471 | B1 | 5/2003 | Heller et al. |
| 6,284,125 | B1 | 9/2001 | Hodges et al. | 6,562,625 | B2 | 5/2003 | Modzelewski et al. |
| 6,284,550 | B1 | 9/2001 | Carroll et al. | 6,565,509 | B1 | 5/2003 | Say et al. |
| 6,287,451 | B1 | 9/2001 | Winarta et al. | 6,565,738 | B1 | 5/2003 | Henning et al. |
| 6,287,595 | B1 | 9/2001 | Loewy et al. | 6,570,390 | B2 | 5/2003 | Hirayama et al. |
| 6,287,875 | B1 | 9/2001 | Geisberg | 6,571,651 | B1 | 6/2003 | Hodges |
| 6,294,281 | B1 | 9/2001 | Heller | 6,572,822 | B2 | 6/2003 | Jurik et al. |
| 6,295,506 | B1 | 9/2001 | Heinonen et al. | 6,574,425 | B1 | 6/2003 | Weiss et al. |
| 6,299,757 | B1 | 10/2001 | Feldman et al. | 6,576,101 | B1 | 6/2003 | Heller et al. |
| 6,300,123 | B1 | 10/2001 | Vadgama et al. | 6,576,117 | B1 | 6/2003 | Iketaki et al. |
| 6,300,142 | B1 | 10/2001 | Andrewes et al. | 6,576,416 | B2 | 6/2003 | Haviland et al. |
| 6,300,961 | B1 | 10/2001 | Finger et al. | 6,576,461 | B2 | 6/2003 | Heller et al. |
| 6,309,526 | B1 | 10/2001 | Fujiwara et al. | 6,579,690 | B1 | 6/2003 | Bonnecaze et al. |
| 6,315,951 | B1 | 11/2001 | Markart | 6,591,125 | B1 | 7/2003 | Buse et al. |

| | | | | | |
|---|---|---|---|---|---|
| 6,592,744 B1 | 7/2003 | Hodges et al. | 2002/0150930 A1 | 10/2002 | Nadaoka et al. |
| 6,592,745 B1 | 7/2003 | Feldman et al. | 2002/0152793 A1 | 10/2002 | Sato et al. |
| 6,594,514 B2 | 7/2003 | Berner et al. | 2002/0155030 A1 | 10/2002 | Matsuda et al. |
| 6,599,406 B1 * | 7/2003 | Kawanaka et al. ..... 204/403.02 | 2002/0155615 A1 | 10/2002 | Novikov et al. |
| 6,600,997 B2 | 7/2003 | Deweese et al. | 2002/0157948 A2 | 10/2002 | Liamos et al. |
| 6,605,200 B1 | 8/2003 | Mao et al. | 2002/0160517 A1 | 10/2002 | Modzelewski et al. |
| 6,605,201 B1 | 8/2003 | Mao et al. | 2002/0164822 A1 | 11/2002 | Takahashi et al. |
| 6,607,658 B1 | 8/2003 | Heller et al. | 2002/0168290 A1 | 11/2002 | Yuzhakov et al. |
| 6,616,819 B1 | 9/2003 | Liamos et al. | 2002/0168298 A1 | 11/2002 | Huhn et al. |
| 6,618,934 B1 | 9/2003 | Feldman et al. | 2002/0175075 A1 | 11/2002 | Deng et al. |
| 6,623,501 B2 | 9/2003 | Heller et al. | 2002/0175087 A1 | 11/2002 | Hodges et al. |
| 6,627,057 B1 | 9/2003 | Bhullar et al. | 2002/0177788 A1 | 11/2002 | Hodges et al. |
| 6,632,349 B1 | 10/2003 | Hodges et al. | 2002/0179440 A1 | 12/2002 | Tokunaga et al. |
| 6,638,415 B1 | 10/2003 | Hodges et al. | 2002/0179441 A1 | 12/2002 | Yamanishi et al. |
| 6,638,716 B2 | 10/2003 | Heller et al. | 2002/0179442 A1 | 12/2002 | Miyazaki et al. |
| 6,645,359 B1 | 11/2003 | Bhullar et al. | 2002/0185385 A1 | 12/2002 | Charlton |
| 6,654,625 B1 | 11/2003 | Say et al. | 2002/0189941 A1 | 12/2002 | Katsuki et al. |
| 6,656,702 B1 | 12/2003 | Yugawa et al. | 2003/0000834 A1 | 1/2003 | Yoshioka et al. |
| 6,676,995 B2 | 1/2004 | Dick et al. | 2003/0024811 A1 | 2/2003 | Davies et al. |
| 6,689,411 B2 | 2/2004 | Dick et al. | 2003/0032875 A1 | 2/2003 | Taniike et al. |
| 6,814,844 B2 * | 11/2004 | Bhullar et al. ......... 204/403.01 | 2003/0036202 A1 | 2/2003 | Teodorcyzk et al. |
| 6,827,829 B2 * | 12/2004 | Kawanaka et al. ..... 204/403.02 | 2003/0042137 A1 | 3/2003 | Mao et al. |
| 6,875,327 B1 | 4/2005 | Miyazaki et al. | 2003/0042150 A1 | 3/2003 | Ryu et al. |
| 7,041,206 B2 | 5/2006 | Gephart et al. | 2003/0054427 A1 | 3/2003 | Phillips et al. |
| 7,388,386 B2 * | 6/2008 | Ramgopal et al. ........... 324/700 | 2003/0064525 A1 | 4/2003 | Liess |
| 7,429,865 B2 * | 9/2008 | Dreibholz et al. ........... 324/692 | 2003/0073151 A1 | 4/2003 | Phillips et al. |
| 7,604,721 B2 * | 10/2009 | Groll et al. ............. 204/403.01 | 2003/0073152 A1 | 4/2003 | Phillips et al. |
| 2001/0006149 A1 | 7/2001 | Taniike et al. | 2003/0073153 A1 | 4/2003 | Phillips et al. |
| 2001/0006150 A1 | 7/2001 | Taniike et al. | 2003/0079987 A1 | 5/2003 | Hodges et al. |
| 2001/0017269 A1 | 8/2001 | Heller et al. | 2003/0080001 A1 | 5/2003 | Hodges et al. |
| 2001/0019831 A1 | 9/2001 | Phillips et al. | 2003/0088166 A1 | 5/2003 | Say et al. |
| 2001/0034068 A1 | 10/2001 | Spivey et al. | 2003/0094383 A1 | 5/2003 | Kermani |
| 2001/0039057 A1 | 11/2001 | Douglas et al. | 2003/0098233 A1 | 5/2003 | Kermani et al. |
| 2001/0041830 A1 | 11/2001 | Varalli et al. | 2003/0098234 A1 | 5/2003 | Hasegawa et al. |
| 2001/0042683 A1 | 11/2001 | Musho et al. | 2003/0100030 A1 | 5/2003 | Nadaoka et al. |
| 2001/0052470 A1 | 12/2001 | Hodges et al. | 2003/0100040 A1 | 5/2003 | Bonnecaze et al. |
| 2001/0053535 A1 | 12/2001 | Bashir et al. | 2003/0100821 A1 | 5/2003 | Heller et al. |
| 2001/0054319 A1 | 12/2001 | Heller et al. | 2003/0102213 A1 | 6/2003 | Gotoh et al. |
| 2002/0003087 A1 | 1/2002 | Chih-hui | 2003/0106809 A1 | 6/2003 | Kermani et al. |
| 2002/0004196 A1 | 1/2002 | Whitson | 2003/0108976 A1 | 6/2003 | Braig et al. |
| 2002/0008038 A1 | 1/2002 | Heller et al. | 2003/0109798 A1 | 6/2003 | Kermani |
| 2002/0019707 A1 | 2/2002 | Cohen et al. | 2003/0132110 A1 | 7/2003 | Hasegawa et al. |
| 2002/0023489 A1 | 2/2002 | Reimelt et al. | 2003/0134347 A1 | 7/2003 | Heller et al. |
| 2002/0025469 A1 | 2/2002 | Heller | 2003/0143113 A2 | 7/2003 | Yuzhakov et al. |
| 2002/0029058 A1 | 3/2002 | LeVaughn et al. | 2003/0143116 A1 | 7/2003 | Zheng et al. |
| 2002/0033345 A1 | 3/2002 | Meade | 2003/0146110 A1 | 8/2003 | Karinka et al. |
| 2002/0040850 A1 | 4/2002 | Liu et al. | 2003/0150724 A1 | 8/2003 | Kawanaka et al. |
| 2002/0042090 A1 | 4/2002 | Heller et al. | 2003/0152823 A1 | 8/2003 | Heller |
| 2002/0043471 A1 | 4/2002 | Ikeda et al. | 2003/0155237 A1 | 8/2003 | Surridge et al. |
| 2002/0044890 A1 | 4/2002 | Black | 2003/0155538 A1 | 8/2003 | Siepmann |
| 2002/0053523 A1 | 5/2002 | Liamos et al. | 2003/0159944 A1 | 8/2003 | Pottgen et al. |
| 2002/0081588 A1 | 6/2002 | De Lumley-woodyear et al. | 2003/0159945 A1 | 8/2003 | Miyazaki et al. |
| 2002/0082797 A1 | 6/2002 | Deweese et al. | 2003/0164293 A1 | 9/2003 | Hodges et al. |
| 2002/0084184 A1 | 7/2002 | Chambers et al. | 2003/0167862 A1 | 9/2003 | Hodges |
| 2002/0084196 A1 | 7/2002 | Liamos et al. | 2003/0168338 A1 | 9/2003 | Gao et al. |
| 2002/0092612 A1 | 7/2002 | Davies et al. | 2003/0175841 A1 | 9/2003 | Watanabe et al. |
| 2002/0100685 A1 | 8/2002 | Huang et al. | 2003/0175946 A1 | 9/2003 | Tokunaga et al. |
| 2002/0102739 A1 | 8/2002 | Nomura et al. | 2003/0176183 A1 | 9/2003 | Drucker et al. |
| 2002/0112969 A1 | 8/2002 | Hodges et al. | 2003/0178322 A1 | 9/2003 | Iyengar et al. |
| 2002/0117404 A1 | 8/2002 | Maxwell et al. | 2003/0179914 A1 | 9/2003 | Tokunaga et al. |
| 2002/0117639 A1 | 8/2002 | Paolini et al. | 2003/0180183 A1 | 9/2003 | Fukuoka et al. |
| 2002/0125145 A1 | 9/2002 | Ohara et al. | 2003/0187338 A1 | 10/2003 | Say et al. |
| 2002/0130042 A1 | 9/2002 | Moerman et al. | 2003/0188427 A1 | 10/2003 | Say et al. |
| 2002/0130043 A1 | 9/2002 | Hodges et al. | 2003/0190069 A1 | 10/2003 | Nikitin et al. |
| 2002/0133064 A1 | 9/2002 | Ueno et al. | 2003/0199744 A1 | 10/2003 | Buse et al. |
| 2002/0137200 A1 | 9/2002 | Takahashi et al. | 2003/0199893 A1 | 10/2003 | Boecker et al. |
| 2002/0137230 A1 | 9/2002 | Nadaoka et al. | 2003/0201194 A1 | 10/2003 | Heller et al. |
| 2002/0138275 A1 | 9/2002 | Amano et al. | 2003/0203498 A1 | 10/2003 | Neel et al. |
| 2002/0138356 A1 | 9/2002 | Dutta et al. | 2003/0203503 A1 | 10/2003 | Fukuoka et al. |
| 2002/0139692 A1 | 10/2002 | Tokunaga et al. | 2003/0217918 A1 | 11/2003 | Davies et al. |
| 2002/0146835 A1 | 10/2002 | Modzelewski et al. | 2004/0005721 A1 | 1/2004 | Tanike et al. |
| 2002/0148726 A1 | 10/2002 | Yamamoto et al. | 2004/0016642 A1 | 1/2004 | Miyazaki et al. |
| 2002/0148739 A2 | 10/2002 | Liamos et al. | 2004/0020777 A1 | 2/2004 | Miyamoto et al. |

| | | | |
|---|---|---|---|
| 2004/0106941 A1 | 6/2004 | Roe et al. | |
| 2004/0134779 A1 | 7/2004 | Hsu et al. | |
| 2004/0216516 A1 | 11/2004 | Sato | |
| 2004/0244151 A1 | 12/2004 | Sakata et al. | |
| 2006/0070878 A1 | 4/2006 | Wu et al. | |
| 2007/0110615 A1* | 5/2007 | Neel et al. | 422/57 |
| 2008/0254544 A1* | 10/2008 | Modzelewski et al. | 436/43 |
| 2009/0125268 A1* | 5/2009 | Perry | 702/100 |

FOREIGN PATENT DOCUMENTS

| | | |
|---|---|---|
| EP | 0 010 456 | 4/1980 |
| EP | 0 034 049 | 8/1981 |
| EP | 0 057 110 | 8/1982 |
| EP | 0 073 056 A2 | 3/1983 |
| EP | 0 084 874 A1 | 8/1983 |
| EP | 0 101 880 | 3/1984 |
| EP | 0 132 790 A2 | 2/1985 |
| EP | 0 164 180 | 12/1985 |
| EP | 0 171 148 | 2/1986 |
| EP | 0 171 239 | 2/1986 |
| EP | 0 186 286 | 7/1986 |
| EP | 0 241 309 A2 | 10/1987 |
| EP | 0 287 883 | 10/1988 |
| EP | 0 359 831 | 3/1990 |
| EP | 0 206 218 B1 | 6/1991 |
| EP | 0 471 986 A2 | 2/1992 |
| EP | 0 471 986 A3 | 4/1992 |
| EP | 0 255 291 B1 | 6/1992 |
| EP | 0 546 536 | 6/1993 |
| EP | 0 244 326 B1 | 8/1993 |
| EP | 0 537 761 A3 | 2/1994 |
| EP | 0 417 796 B1 | 11/1994 |
| EP | 0 213 343 B2 | 2/1995 |
| EP | 0 636 880 A2 | 2/1995 |
| EP | 0 640 832 A | 3/1995 |
| EP | 0 651 250 A2 | 5/1995 |
| EP | 0 471 986 B1 | 10/1995 |
| EP | 0 127 958 B2 | 4/1996 |
| EP | 0 732 406 A1 | 9/1996 |
| EP | 0 732 590 A2 | 9/1996 |
| EP | 0 383 322 B1 | 2/1997 |
| EP | 0 537 761 B1 | 8/1997 |
| EP | 0 840 122 A2 | 5/1998 |
| EP | 0 851 224 | 7/1998 |
| EP | 0 859 230 | 8/1998 |
| EP | 0 878 713 | 11/1998 |
| EP | 0 837 320 A3 | 12/1998 |
| EP | 0 887 421 A1 | 12/1998 |
| EP | 0 894 509 A2 | 2/1999 |
| EP | 0 470 649 B1 | 6/1999 |
| EP | 0 942 278 A2 | 9/1999 |
| EP | 0 964 059 | 12/1999 |
| EP | 0 987 544 | 3/2000 |
| EP | 1 024 358 A1 | 8/2000 |
| EP | 1 035 216 A1 | 9/2000 |
| EP | 0 230 472 B2 | 12/2000 |
| EP | 1 067 384 A2 | 1/2001 |
| EP | 1 074 832 A1 | 2/2001 |
| EP | 1 081 490 A1 | 3/2001 |
| EP | 1 130 390 A1 | 9/2001 |
| EP | 0 741 186 B1 | 10/2001 |
| EP | 1 143 245 | 10/2001 |
| EP | 1 147 739 A2 | 10/2001 |
| EP | 1 152 239 A1 | 11/2001 |
| EP | 1 156 324 | 11/2001 |
| EP | 1 225 448 | 7/2002 |
| EP | 1 235 069 A1 | 8/2002 |
| EP | 0 958 495 | 11/2002 |
| EP | 1 102 991 B1 | 11/2002 |
| EP | 1 256 798 | 11/2002 |
| EP | 1 275 732 | 1/2003 |
| EP | 1 281 955 | 2/2003 |
| EP | 1 009 850 B1 | 3/2003 |
| EP | 1 288 653 A1 | 3/2003 |
| EP | 1 312 919 A2 | 5/2003 |
| EP | 1 316 367 | 6/2003 |
| EP | 1 318 396 A1 | 6/2003 |
| EP | 0 876 506 | 7/2003 |
| EP | 1 129 211 B1 | 7/2003 |
| EP | 1 308 720 A1 | 7/2003 |
| EP | 1 324 025 A2 | 7/2003 |
| EP | 1 324 038 | 7/2003 |
| EP | 1 327 881 | 7/2003 |
| EP | 1 352 611 A1 | 10/2003 |
| EP | 1 352 969 | 10/2003 |
| EP | 1 369 684 | 12/2003 |
| EP | 1 369 687 | 12/2003 |
| EP | 1 119 637 | 3/2004 |
| EP | 1 394 535 | 3/2004 |
| EP | 1 413 879 | 4/2004 |
| EP | 1 431 758 A1 | 6/2004 |
| GB | 2 295 676 | 6/1996 |
| GB | 2 365 123 | 2/2002 |
| JP | 63-111453 | 5/1988 |
| JP | 63-128252 | 5/1988 |
| JP | 01-291153 | 11/1989 |
| JP | 03-099254 | 4/1991 |
| JP | 04-121652 | 4/1992 |
| JP | 93-312761 | 11/1993 |
| JP | 08-262026 | 10/1996 |
| JP | 09-043242 | 2/1997 |
| JP | 91-59644 | 6/1997 |
| JP | 10 332626 | 12/1998 |
| JP | 2000-19146 | 1/2000 |
| JP | 2000 019147 | 1/2000 |
| JP | 200019147 A | 1/2000 |
| JP | 2001-021526 | 1/2001 |
| JP | 2002-156358 A | 5/2002 |
| RU | 2180514 | 3/2002 |
| WO | WO 81/01794 | 7/1981 |
| WO | WO 83/00926 | 3/1983 |
| WO | WO 86/07632 | 12/1986 |
| WO | WO 89/08713 | 9/1989 |
| WO | WO 89/09397 | 10/1989 |
| WO | WO 90/05293 | 5/1990 |
| WO | WO 92/01928 | 2/1992 |
| WO | WO 92/07655 | 5/1992 |
| WO | WO 92/15859 | 9/1992 |
| WO | WO 92/15861 | 9/1992 |
| WO | WO 92/15950 | 9/1992 |
| WO | WO 92/22669 | 12/1992 |
| WO | WO 93/09433 | 5/1993 |
| WO | WO 94/12950 | 6/1994 |
| WO | WO 94/16095 | 7/1994 |
| WO | WO 94/23295 | 10/1994 |
| WO | WO 94/28414 | 12/1994 |
| WO | WO 94/29705 | 12/1994 |
| WO | WO 95/03542 | 2/1995 |
| WO | WO 95/06919 | 3/1995 |
| WO | WO 95/07050 | 3/1995 |
| WO | WO 95/22597 | 8/1995 |
| WO | WO 96/04398 | 2/1996 |
| WO | WO 96/07908 | 3/1996 |
| WO | WO 96/13707 | 5/1996 |
| WO | WO 96/15454 | 5/1996 |
| WO | WO 96/33403 | 10/1996 |
| WO | WO 97/00441 | 1/1997 |
| WO | WO 97/02487 | 1/1997 |
| WO | WO 97/08544 | 3/1997 |
| WO | WO 97/16726 | 5/1997 |
| WO | WO 97/18465 | 5/1997 |
| WO | WO 97/29366 | 8/1997 |
| WO | WO 97/29847 | 8/1997 |
| WO | WO 97/30344 | 8/1997 |
| WO | WO 97/39341 | 10/1997 |

| | | |
|---|---|---|
| WO | WO 97/39343 | 10/1997 |
| WO | WO 97/42882 | 11/1997 |
| WO | WO 97/42888 | 11/1997 |
| WO | WO 97/45719 | 12/1997 |
| WO | WO 98/05424 | 2/1998 |
| WO | WO 98/19153 | 5/1998 |
| WO | WO 98/19159 | 5/1998 |
| WO | WO 98/29740 | 7/1998 |
| WO | WO 98/35225 | 8/1998 |
| WO | WO 98/55853 | 12/1998 |
| WO | WO 98/57159 | 12/1998 |
| WO | WO 99/05966 | 2/1999 |
| WO | WO 99/09404 | 2/1999 |
| WO | WO 99/12008 | 3/1999 |
| WO | WO 99/12021 | 3/1999 |
| WO | WO 99/13099 | 3/1999 |
| WO | WO 99/13100 | 3/1999 |
| WO | WO 99/05516 | 4/1999 |
| WO | WO 99/22236 | 5/1999 |
| WO | WO 99/23479 | 5/1999 |
| WO | WO 99/29230 | 6/1999 |
| WO | WO 99/30152 | 6/1999 |
| WO | WO 99/32881 | 7/1999 |
| WO | WO 99/39627 | 8/1999 |
| WO | WO 99/41596 | 8/1999 |
| WO | WO 99/51974 | 10/1999 |
| WO | WO 99/57317 | 11/1999 |
| WO | WO 99/58709 | 11/1999 |
| WO | WO 99/59464 | 11/1999 |
| WO | WO 99/60383 | 11/1999 |
| WO | WO 99/64620 | 12/1999 |
| WO | WO 00/09996 | 2/2000 |
| WO | WO 00/10007 | 2/2000 |
| WO | WO 00/20626 | 4/2000 |
| WO | WO 00/26638 | 5/2000 |
| WO | WO 00/28068 | 5/2000 |
| WO | WO 00/33072 | 6/2000 |
| WO | WO 00/33074 | 6/2000 |
| WO | WO 00/42422 | 7/2000 |
| WO | WO 00/45160 | 8/2000 |
| WO | WO 00/54047 | 9/2000 |
| WO | WO 00/57177 | 9/2000 |
| WO | WO 00/60340 | 10/2000 |
| WO | WO 00/62047 | 10/2000 |
| WO | WO 00/73778 | 12/2000 |
| WO | WO 00/73785 A2 | 12/2000 |
| WO | WO 00/78917 A1 | 12/2000 |
| WO | WO 00/078992 | 12/2000 |
| WO | WO 01/02093 A2 | 1/2001 |
| WO | WO 01/13115 A2 | 2/2001 |
| WO | WO 01/13115 A3 | 2/2001 |
| WO | WO 01/25775 | 4/2001 |
| WO | WO 01/25776 | 4/2001 |
| WO | WO 01/28423 | 4/2001 |
| WO | WO 01/73420 A1 | 4/2001 |
| WO | WO 01/30915 | 5/2001 |
| WO | WO 01/33216 A1 | 5/2001 |
| WO | WO 01/36430 | 5/2001 |
| WO | WO 01/36660 | 5/2001 |
| WO | WO 01/36953 A1 | 5/2001 |
| WO | WO 01/46457 A2 | 6/2001 |
| WO | WO 01/40788 | 7/2001 |
| WO | WO 01/57238 | 8/2001 |
| WO | WO 01/57239 | 8/2001 |
| WO | WO 01/57510 | 8/2001 |
| WO | WO 01/64105 | 9/2001 |
| WO | WO 01/67099 A1 | 9/2001 |
| WO | WO 01/71328 A1 | 9/2001 |
| WO | WO 01/71329 | 9/2001 |
| WO | WO 01/72220 | 10/2001 |
| WO | WO 01/73109 | 10/2001 |
| WO | WO 01/73114 | 10/2001 |
| WO | WO 01/73124 | 10/2001 |
| WO | WO 01/73395 | 10/2001 |
| WO | WO 01/74242 | 10/2001 |
| WO | WO 01/75433 | 10/2001 |
| WO | WO 01/75438 A2 | 10/2001 |
| WO | WO 01/84133 A1 | 11/2001 |
| WO | WO 01/84142 | 11/2001 |
| WO | WO 01/88524 | 11/2001 |
| WO | WO 01/92857 | 12/2001 |
| WO | WO 01/95806 | 12/2001 |
| WO | WO 01/96596 | 12/2001 |
| WO | WO 02/00112 A2 | 1/2002 |
| WO | WO 02/06822 | 1/2002 |
| WO | WO 02/08750 | 1/2002 |
| WO | WO 02/08753 A2 | 1/2002 |
| WO | WO 02/10728 | 2/2002 |
| WO | WO 02/13966 | 2/2002 |
| WO | WO 02/13970 | 2/2002 |
| WO | WO 02/14535 | 2/2002 |
| WO | WO 02/18053 A1 | 3/2002 |
| WO | WO 02/22855 | 3/2002 |
| WO | WO 02/32559 | 4/2002 |
| WO | WO 02/48707 | 6/2002 |
| WO | WO 02/49507 | 6/2002 |
| WO | WO 02/50609 | 6/2002 |
| WO | WO 02/054055 A1 | 7/2002 |
| WO | WO 02/057767 A1 | 7/2002 |
| WO | WO 02/057768 | 7/2002 |
| WO | WO 02/057781 | 7/2002 |
| WO | WO 02/058537 | 8/2002 |
| WO | WO 02/062212 | 8/2002 |
| WO | WO 02/067768 | 9/2002 |
| WO | WO 02/070734 A1 | 9/2002 |
| WO | WO 02/071044 | 9/2002 |
| WO | WO 02/078512 A2 | 10/2002 |
| WO | WO 02/078533 | 10/2002 |
| WO | WO 02/086483 | 10/2002 |
| WO | WO 02/093152 | 11/2002 |
| WO | WO 02/095355 | 11/2002 |
| WO | WO 02/097418 | 12/2002 |
| WO | WO 02/103343 A1 | 12/2002 |
| WO | WO 03/005015 | 1/2003 |
| WO | WO 03/012422 | 2/2003 |
| WO | WO 03/014740 A1 | 2/2003 |
| WO | WO 03/014741 A1 | 2/2003 |
| WO | WO 03/015627 | 2/2003 |
| WO | WO 03/015629 | 2/2003 |
| WO | WO 03/021706 A1 | 3/2003 |
| WO | WO 03/025257 | 3/2003 |
| WO | WO 03/029804 | 4/2003 |
| WO | WO 03/029804 A1 | 4/2003 |
| WO | WO 03/032411 | 4/2003 |
| WO | WO 03/039483 A2 | 5/2003 |
| WO | WO 03/042679 A1 | 5/2003 |
| WO | WO 03/042680 A1 | 5/2003 |
| WO | WO 03/044513 | 5/2003 |
| WO | WO 03/048756 A1 | 6/2003 |
| WO | WO 03/060154 A2 | 7/2003 |
| WO | WO 03/067252 | 8/2003 |
| WO | WO 03/069304 A2 | 8/2003 |
| WO | WO 03/083469 | 10/2003 |
| WO | WO 03/085372 | 10/2003 |
| WO | WO 03/091717 | 11/2003 |
| WO | WO 2004/005908 | 1/2004 |

OTHER PUBLICATIONS

Aoki et al., "Quantitative Analysis of Reversible Diffusion Controlled Currents of Redox Soluble Species at Interdigitated Array Electrodes Under Steady-State Conditions", J. Electroanal. Chem. 256 (1988) 269-282.

Aoki et al., "Time-Dependence of Diffusion-Controlled Currents of a Soluble Redox Couple at Interdigitated Microarray Electrodes". J. Electronanal. Chem. 266 (1989) 11-20.

Bartlett, P.N. and Whitaker, R.G., "Electrochemical Immobilisation of Enzymes: Part I. Theory", J. Electroanal Chem., 224 (1987) 27-35.

Bartlett, P.N. and Whitaker, R.G., "Electrochemical Immobilisation of Enzymes: Part II. Glucose Oxidase Immobilised in Poly-N-Methylpyrrole", J. Electroanal. Chem., 224 (1987) 37-48.

Beyer et al., "Development and Application of a New Enzyme Sensor Type Based on the EIS-Capacitance Structure for Bioprocess Control," Biosensors & Bioelectronics, vol. 9, pp. 17-21 (1994).

Bradley et al., "Kinetic Analysis of Enzyme Electrode Response," Anal. Chem., vol. 56, pp. 664-667 (1984).

Burke, et al., Improved-Accuracy Biosensor Strip for AccuChek™ Advantage®, Presented Orally at ACS Boston Meeting (~1993-1994).

Cardosi et al., "The Realization of Electron Transfer from Biological Molecules to Electrodes,"Biosensors Fundamentals and Applications, chapt. 15 (Turner et al. eds., Oxford University Press. 1987).

Cass et al., "Ferrocene-Mediated Enzyme Electrode for Amperometric Determination of Glucose," Anal. Chem, vol. 56, pp. 667-671 (1984).

Chiba, K.; Ohsaka, T.; Ohnuki, Y.; and Oyama, N., "Electrochemical Preparation of a Ladder Polymer Containing Phenazine Rings." J. Eleectroanal Chemo., 219 (1987) 117-124.

Gebhardt, et al., "Electrocatalytic Glucose Sensor," Siemens Forsch-u, Entwickl-Ber. Bd., vol. 12, pp. 91-95 (1983).

Gregg, et al., "Cross-Lined Redox Gels Containing Glucose Oxidase for Amperometric Biosensor Applications", Anal. Chem. 1990, 62, 258-263.

Hintsche, R. et al., "Chip Biosensors on Thin-Film Metal Electrodes", Sensors and Actuators B. 4 (1991) 287-291.

Ho et al., "Electrochemical Sensor for Measurement of Urea and Creatinine in Serum Based on AC Impedance Measurement of Enzyme-Catalyzed Polymer Transformation." Analytical Chemistry, vol. 71, No. 10, May 15, 1999.

Jin et al., "Application of the Finite Analytic Numerical Method. Part 1. Diffusion Problems on Coplanar an dElevated Interdigitated Microarray Band Electrodes" J. Electroanal. Chem. 441 (1996) 29-36.

Kasapbasioglu et al., "An Impedance Based Ultra-Thin Platinum Island Film Glucose Sensor," Sensor and Actuators B. vol. 13-14, pp. 749-451 (1993).

Koichi, "Measurements of Current-Potential Curves, 6, Cottrell Equation and its Analogs. What Can We Known from Chronoamperometry?" Denki Kagaku ovopi Kogyo Butsuri Kagaku, vol. 54, No. 6, pp. 471-475 (1986).

Lambda Physik Brochure for LPZ® Series.

Lee, et al., "A New Glucose Sensor Using Microporous Enzyme Membrane", Sensors and Actuators B, 3 (1991) 215-219.

Lifescan Guide Entitled "Quick Start" for the Onetouch® Ultra™ Blood Glucose Monitoring System.

Lifescan Owner's Booklet Entitled "The Comfort of Control".

Lifescan Product Brochure for Onetouch® Ultra™ Blood Glucose Monitoring System.

Lifescan Product Brochure for Onetouch® Ultra™ Test Strip.

Malitesta, et al., "Glucose Fast-Response Amperometric Sensor Based on Glucose Oxidase Immobilized in an Electpolymerized Poly (O-Phenylenediamine) Film", Anal. Chem. 1990, 62, 2735-2740.

Meier, et al., "Sensor and Sensor Elements Manufacturing: Laser Direct Patterning (LDP) for Reel to Reel Processing to generate High Throughput", LPKF Laser & Electronics AG, pp. 1-6.

Mell, et al., "A Model for the Amperometric Enzyme Electrode Obtained Through Digital Simulation and Applied to the immobilized Glucose Oxidase System," Analytical Chemistry, vol. 47, pp. 299-307 (Feb. 1975).

Mell et al., "Amperometric Response Enhancement of the Immobilized Glucose Oxidase Enzyme Electrode", Analytical Chemistry, vol. 48, pp. 1597-1601 (Sep. 1976).

Miao et al., "Amperometric Glucose Biosensor Based on Immobilization of Glucose Oxidase in Chitosan dMartrix Cross-Linked With Glutaraldehyde", Electroanalysis 2001, 13, No. 4, 347-349.

Mohri, et al., "Characteristic Response of Electrochemical Nonlinearity to Taste Compounds with a Gold Electrode Modified with 4-Aminobenzenethiol," Bull, Chem. Soc. Jon., vol. 66, pp. 1328-1332 (1993).

Morris, et al., "An Electrochemical Capillary Fill Device for the Analysis of Glucose Incorporating Glucose Oxidase and Ruthenium (III) Hexamine as Mediator," Electroanalysis, vol. 4, pp. 1-9 (1992).

Muller et al., "Influence of Hematocrit and Platelet Count on Impedance and Reactivity of Whole Blood for Electrical Aggregometry," Journal of Pharmacological and Toxicological Methods, vol. 34, pp. 17-22 (1995).

Myland et al., "Membrane-Covered Oxygen Sensors: An Exact Treatment of the Switch-on Transient," Journal of the Electrochemical Society, vol. 131, pp. 1815-1823 (Aug. 1984).

Nishihara et al., "Interdigitated Array Electrode Diffusion Measurements in Donor/Acceptor Solutions in Polyether Electrolyte Solvents", Anal. Chem. 1991, 63, 2955-2960.

Niwa et al., "Electrochemical Behavior of Reversible Redox Species at Interdigitated Array Electrodes With Different Geometries: Consideration of Redox Cycling and Collection Efficiency" Anal. Chem. 62 (1990) 447-452.

Paeschke et al., "Properties of Interdigital Electrode Arrays With Different Geometries", Analytica Chimica Acta 305 (1995) 126-136.

Preidel et al. "Glucose Measurements by Electrocatalytic Sensor in the Extracorporeal Blood Circulation of a Sheep," Sensors and Actuators B, vol. 2, pp. 257-263 (1990).

Preidel et al. "In Vitro Measurements with Electrocatalytic Glucose Sensor in Blood," Biomed. Biochim. Acta, vol. 48, pp. 897-903 (1989).

Saeger et al., "Influence of Urea on the Glucose Measurement by Electrocatalytic Sensor in the Extracorporeal Blood Circulation of a Sheep," Biomed. Biochim. Acta, vol. 50, pp. 885-891 (1991).

Talbott, et al., "A New Microchemical Approach to Amperometric Analysis," Microchemical Journal, vol. 37, pp. 5-12 (1988).

Tender et al., "Electrochemical Patterning of Self-Assembled Monolayers onto Microscopic Arrays of Gold Electrodes Fabricated by Laser Ablation," American Chemical Society, Langmuir, vol. 12, No. 23, pp. 5515-5518, (1996).

Vorburger et al., "In the Rough," National Institute of Standards and Technology, and Ndubuisi Orji, University of North Carolina, Spie's oe magazine, pp. 31-34, (2002).

Williams et al., "Electrochemical-Enzymatic Analysis of Blood Glucose and Lactate." Analytical Chemistry, vol. 42, No. 1, pp. 118-121 (Jan. 1970).

Wollenberger et al., "Interdigitated Array Microelectrodes for the Determination of Enzyme Activities", Analyst, Jun. 1994, 1245-1249.

Zhao, "Contributions of Suspending Medium to Electrical Impedance of Blood," Biochimica et Biophysica Acta, vol. 1201, pp. 179-185 (1994).

Zhao, "Electrical Impedance and Haematocrit of Human Blood with Various Anticoagulants," Physiol. Meas., vol. 14, pp. 299-307 (1993).

http://216.239.41.104/search?q=cache:oNNpSzoOXvgJ:www.future-fab.com, "Introduction", Future Fab International, Montgomery Research, Inc., pp. 1-10, (Jan. 2004).

http://216.239.41.104/search?q=cache: bEmigi1MhtUJ:www.coe.uncc.edu, "LER", Ndubuisi George Orji, pp. 1-3 (Jan. 2004).

http://www.circuittree.com, Vaucher et al., "Laser Direct Imaging and Structuring: An Update", posted on Aug. 2002, pp. 1-6 (Nov. 2003).

http://www.ifm.liu.se/App1phys/ftir/sams.html, "Self-Assembled Monolayers", pp. 1-5 (Jan. 2004).

http://www.tamsci.com/library/news-05-DECEMBER-2002.html, "Patterning Thin Film Circuits at the Speed of Light", Press Release, pp. 1-2 (Nov. 2003).

http://www.zurich.ibm.com/~bmi/samtech.html, "Technological Application of Self-Assembled Monolayers", pp. 1-2 (Jan. 2004).

US 6,517,703, 02/2003, Beaty et al. (withdrawn)

* cited by examiner

| # | C1 | C2 | C3 | C4 | C5 | B1 | B2 |
|---|----|----|----|----|----|------|------|
| 0 | 0 | 0 | 0 | 0 | 0 | - | - |
| 1 | 0 | 0 | 0 | 1 | 0 | - | DC |
| 2 | 0 | 0 | 1 | 0 | 0 | - | C |
| 3 | 0 | 1 | 0 | 1 | 0 | DC/B2 | DC/B1 |
| 4 | 0 | 1 | 1 | 0 | 0 | C/B2 | C/B1 |
| 5 | 1 | 0 | 0 | 0 | 0 | DC | - |
| 6 | 1 | 0 | 1 | 0 | 0 | DC | C |
| 7 | 0 | 0 | 0 | 0 | 1 | C | - |
| 8 | 0 | 1 | 0 | 0 | 0 | B2 | B1 |

Fig. 3

SYSTEM AND METHOD FOR CODING INFORMATION ON A BIOSENSOR TEST STRIP

REFERENCE TO RELATED APPLICATIONS

This application is related to an application titled BIOSENSOR AND METHOD OF MAKING (U.S. patent application Ser. No. 10/871,937, filed Jun. 18, 2004) which is incorporated herein by reference in its entirety. This application claims the benefit of U.S. Provisional Application No. 60/480,199, filed Jun. 20, 2003, the contents of which are hereby incorporated by reference herein.

TECHNICAL FIELD OF THE INVENTION

The present invention relates to an apparatus for use in measuring concentrations of an analyte in a biological fluid. The invention relates more particularly to a system and method for coding information on a biosensor test strip.

BACKGROUND OF THE INVENTION

Measuring the concentration of substances in biological fluids is an important tool for the diagnosis and treatment of many medical conditions. For example, the measurement of glucose in body fluids, such as blood, is crucial to the effective treatment of diabetes.

Diabetic therapy typically involves two types of insulin treatment: basal, and meal-time. Basal insulin refers to continuous, e.g. time-released insulin, often taken before bed. Meal-time insulin treatment provides additional doses of faster acting insulin to regulate fluctuations in blood glucose caused by a variety of factors, including the metabolization of sugars and carbohydrates. Proper regulation of blood glucose fluctuations requires accurate measurement of the concentration of glucose in the blood. Failure to do so can produce extreme complications, including blindness and loss of circulation in the extremities, which can ultimately deprive the diabetic of use of his or her fingers, hands, feet, etc.

Multiple methods are known for determining the concentration of analytes in a blood sample, such as, for example, glucose. Such methods typically fall into one of two categories: optical methods and electrochemical methods. Optical methods generally involve spectroscopy to observe the spectrum shift in the fluid caused by concentration of the analyte, typically in conjunction with a reagent that produces a known color when combined with the analyte. Electrochemical methods generally rely upon the correlation between a current (Amperometry), a potential (Potentiometry) or accumulated charge (Coulometry) and the concentration of the analyte, typically in conjunction with a reagent that produces charge-carriers when combined with the analyte. See, for example, U.S. Pat. No. 4,233,029 to Columbus, U.S. Pat. No. 4,225,410 to Pace, U.S. Pat. No. 4,323,536 to Columbus, U.S. Pat. No. 4,008,448 to Muggli, U.S. Pat. No. 4,654,197 to Lilja et al., U.S. Pat. No. 5,108,564 to Szuminsky et al., U.S. Pat. No. 5,120,420 to Nankai et al., U.S. Pat. No. 5,128,015 to Szuminsky et al., U.S. Pat. No. 5,243,516 to White, U.S. Pat. No. 5,437,999 to Diebold et al., U.S. Pat. No. 5,288,636 to Pollmann et al., U.S. Pat. No. 5,628,890 to Carter et al., U.S. Pat. No. 5,682,884 to Hill et al., U.S. Pat. No. 5,727,548 to Hill et al., U.S. Pat. No. 5,997,817 to Crismore et al., U.S. Pat. No. 6,004,441 to Fujiwara et al., U.S. Pat. No. 4,919,770 to Priedel, et al., and U.S. Pat. No. 6,054,039 to Shieh, which are hereby incorporated in their entireties. The biosensor for conducting the tests is typically a disposable test strip having a reagent thereon that chemically reacts with the analyte of interest in the biological fluid. The test strip is mated to a nondisposable test meter such that the test meter can measure the reaction between the analyte and the reagent in order to determine and display the concentration of the analyte to the user.

It is common practice in such test meter/test strip systems to ensure proper identification of the test strip in order to ensure proper test results. For example, a single test meter may be able to analyze several different types of test strips, wherein each type of test strip is designed to test for the presence of a different analyte in the biological fluid. In order to properly conduct the test, the test meter must know which type of test is to be performed for the test strip currently in use.

Also, lot-to-lot variations in the test strips normally require calibration information to be loaded into the test meter in order to ensure accurate test results. A common practice for downloading such calibration information into the test meter is the use of an electronic read-only memory key (ROM key) that is inserted into a socket of the test meter. Because this calibration data may only be accurate for a particular production lot of test strips, the user is usually asked to confirm that the lot number of the test strip currently in use matches the lot number for which the ROM key was programmed.

Many other instances in which it is desirable to have information relating to the test strip are known to those having skill in the art. Prior art attempts to code information onto the test strip for reading by the test meter have suffered from many problems, including a severely limited amount of information that can be coded and the use of relatively large amounts of test strip surface area for the information coding function.

Thus, a system and method are needed that will allow information to be coded onto a biosensor for reading of the information by the test meter. The present invention is directed toward meeting this need.

SUMMARY OF THE INVENTION

The present invention provides a test strip for measuring a concentration of an analyte of interest in a biological fluid, wherein the test strip may be encoded with information that can be read by a test meter into which the test strip is inserted.

In one form of the invention, a method for forming a test strip for measuring a concentration of an analyte of interest in a biological fluid is disclosed, the method comprising the steps of: providing a basic test strip design comprising: a substrate having a surface and at least one measurement electrode formed thereon; a plurality of conductive contact pads formed upon the substrate surface, including at least one information contact pad and at least one measurement contact pad; and a plurality of potential conductive links conductively coupling various ones of the plurality of contact pads; wherein the at least one information contact pad is not coupled to any of the at least one measurement electrodes except by one or more of the plurality of potential conductive links, and the at least one measurement contact pad is coupled to one of the at least one measurement electrodes by a path other than one or more of the plurality of potential conductive links; defining a set of valid test strip designs; wherein each one of the set of valid test strip designs incorporates none, one or more than one of the plurality of potential conductive links; and wherein at least one of the plurality of potential conductive links couples a first one of the information contact pads to a first one of the measurement contact pads in a first valid test strip design, and at least one of the plurality of potential conductive links couples the first one of the information contact pads to a second one of the measurement contact pads in a second valid test strip design; selecting one design from the set of valid test strip designs; and forming a test strip per said selected one design.

In another form of the invention, a plurality of test strips for measuring a concentration of an analyte of interest in a biological fluid is disclosed, each of the plurality of test strips being substantially identical to one another except for a presence or absence of a plurality of potential conductive links, at least one of the test strips comprising: a substrate having a surface and at least one measurement electrode formed thereon; a plurality of conductive contact pads formed upon the substrate surface, including at least one information contact pad and at least one measurement contact pad; and a plurality of conductive links selected from the plurality of potential conductive links, wherein the plurality of conductive links conductively couple at least three contact pads together; wherein the at least one information contact pad is not coupled to any of the at least one measurement electrodes except by one or more of the plurality of potential conductive links, and the at least one measurement contact pad is coupled to one of the at least one measurement electrodes by a path other than one or more of the plurality of potential conductive links.

In another form of the invention, a method for forming a test strip for measuring a concentration of an analyte of interest in a biological fluid is disclosed, the method comprising the steps of: providing a basic test strip design comprising: a substrate having a surface and at least one measurement electrode formed thereon; a plurality of conductive contact pads formed upon the substrate surface, including at least one information contact pad and at least one measurement contact pad; and a plurality of potential conductive links conductively coupling various ones of the plurality of contact pads; wherein the at least one information contact pad is not coupled to any of the at least one measurement electrodes except by one or more of the plurality of potential conductive links, and the at least one measurement contact pad is coupled to one of the at least one measurement electrodes by a path other than one or more of the plurality of potential conductive links; defining a set of valid test strip designs; wherein each one of the set of valid test strip designs incorporates none, one or more than one of the plurality of potential conductive links; and wherein at least one of the set of valid test strip designs includes conductive links that conductively couple at least three contact pads together; selecting one design from the set of valid test strip designs; and forming a test strip per said selected one design.

In another form of the invention, a test strip for measuring a concentration of an analyte of interest in a biological fluid is disclosed, the test strip comprising: a substrate having a surface and at least one measurement electrode formed thereon; a plurality of conductive contact pads formed upon the substrate surface, including at least one information contact pad and at least one measurement contact pad; and at least one conductive link conductively coupling at least three of the contact pads; wherein the at least one information contact pad is not coupled to any of the at least one measurement electrodes except by one or more of the at least one conductive links, and the at least one measurement contact pad is coupled to one of the at least one measurement electrodes by a path other than one or more of the at least one conductive links.

In another form of the invention, a test strip for measuring a concentration of an analyte of interest in a biological fluid is disclosed, the test strip comprising: a substrate having a surface and at least one measurement electrode formed thereon; a plurality of conductive contact pads formed upon the substrate surface, including at least one information contact pad and at least one measurement contact pad; and at least one conductive link conductively coupling at least three of the contact pads; wherein the at least one information contact pad is not coupled to any of the at least one measurement electrodes except by one or more of the at least one conductive links, and the at least one measurement contact pad is coupled to one of the at least one measurement electrodes by a path other than one or more of the at least one conductive links.

In another form of the invention, a test strip for measuring a concentration of an analyte of interest in a biological fluid is disclosed, the test strip adapted to be inserted into a test meter having at least one connector contact that touches the inserted test strip, the test strip comprising: a substrate having a top surface; a conductive layer formed on at least a portion of the substrate top surface; and at least one predetermined contact pad position defined upon the substrate top surface; wherein each of the at least one contact pad positions is touched by a respective one of the at least one connector contacts when the at least one connector contacts touch the test strip; wherein a presence of the conductive layer in a respective one of the contact pad positions is operative to indicate a first state of a binary bit to the test meter; and wherein an absence of the conductive layer in a respective one of the contact pad positions is operative to indicate a second state of a binary bit to the test meter.

In another form of the invention, a method for measuring a concentration of an analyte of interest in a biological fluid, comprising the steps of: providing a test meter having at least one connector contact that touches an inserted test strip, providing a test strip adapted to be inserted into the test meter, the test strip comprising: a substrate having a top surface; a conductive layer formed on at least a portion of the substrate top surface; and at least one predetermined contact pad position defined upon the substrate top surface; touching each of the at least one predetermined contact pad positions with a respective one of the at least one connector contacts; indicating a first state of a binary bit within the test meter in response to a presence of the conductive layer in a respective one of the contact pad positions; and indicating a second state of a binary bit within the test meter in response to an absence of the conductive layer in a respective one of the contact pad positions.

BRIEF DESCRIPTION OF THE DRAWINGS

The invention will be further described, by way of example only, with reference to the accompanying drawings, in which:

FIG. 3 is a table showing a first embodiment coding sequence for the test strip of FIG. 2.

DETAILED DESCRIPTION OF THE PREFERRED EMBODIMENTS

Figure 1:
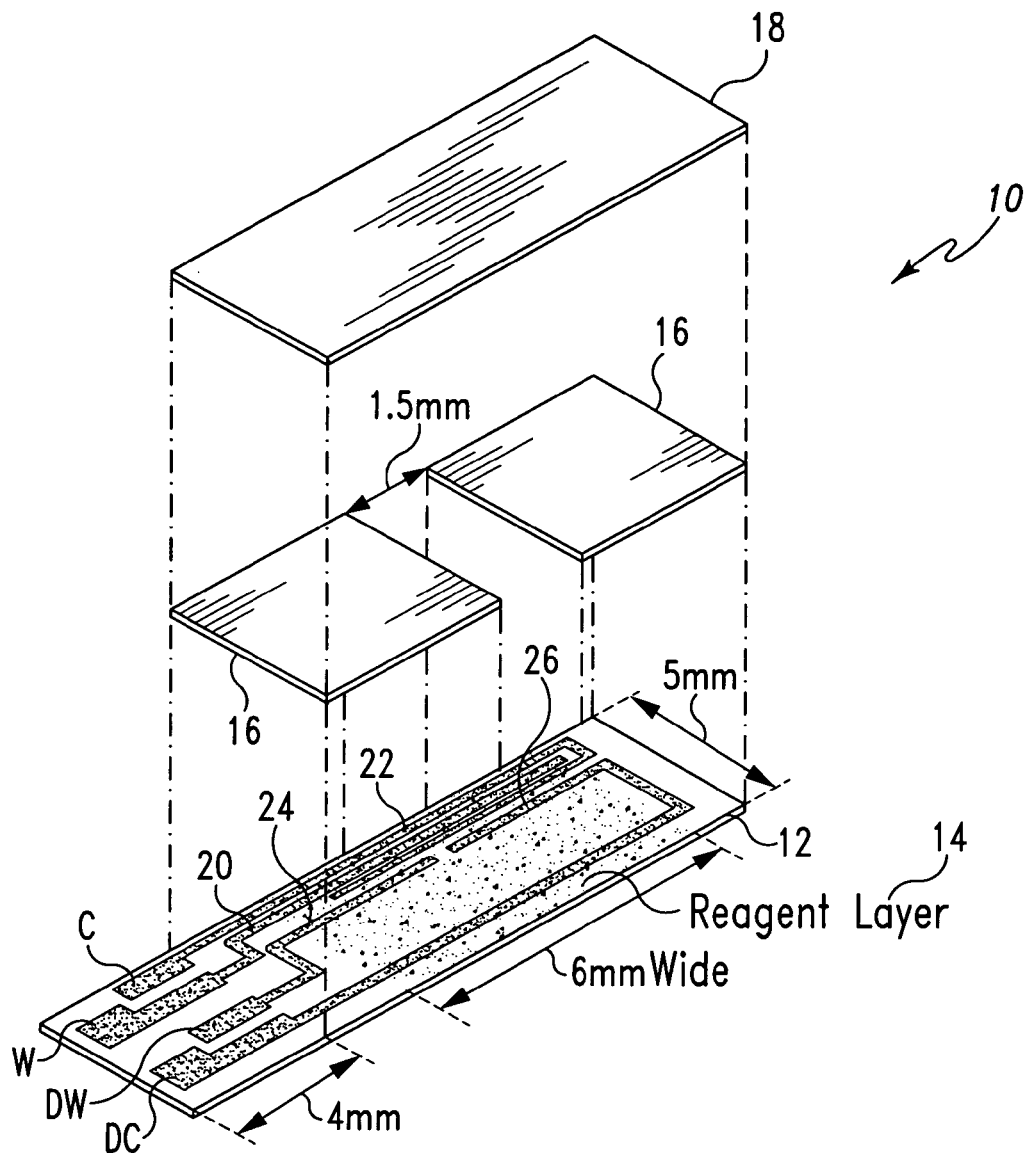
FIG. 1 is an exploded perspective view of a first typical test strip for use in measuring the concentration of an analyte of interest in a biological fluid.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. In particular, although the invention is discussed in terms of a blood glucose meter, it is contemplated that the invention can be used with devices for measuring other analytes and other sample types. Such alternative embodiments require certain adaptations to the embodiments discussed herein that would be obvious to those skilled in the art.

Although the system and method of the present invention may be used with test strips having a wide variety of designs and made with a wide variety of construction techniques and processes, a typical electrochemical test strip is illustrated in FIG. 1, and indicated generally at 10. Referring to FIG. 1, the test strip 10 comprises a bottom substrate 12 formed from an opaque piece of 350 μm thick polyester (such as Melinex 329 available from DuPont) coated on its top surface with a 50 nm conductive (gold) layer (by sputtering or vapor deposition, for example). Electrodes, connecting traces and contact pads therefor are then patterned in the conductive layer by a laser ablation process. The laser ablation process is performed by means of an excimer laser which passes through a chrome-on-quartz mask. The mask pattern causes parts of the laser field to be reflected while allowing other parts of the field to pass through, creating a pattern on the gold which is ablated where contacted by the laser light. The laser ablation process is described in greater detail hereinbelow. For example, working 20, counter 22, dose sufficiency working 24, and dose sufficiency counter 26 electrodes may be formed as shown and coupled, respectively, to measurement contact pads W, C, DW and DC. These contact pads provide a conductive area upon the test strip 10 to be contacted by a connector contact of the test meter once the test strip 10 is inserted into the test meter.

The bottom substrate 12 is then coated in the area extending over the electrodes with a reagent layer 14 as a continuous, extremely thin reagent film. The reagent layer 14 is a stripe of approximately 6 millimeters width across the substrate 12 in the region labeled "Reagent Layer" on FIG. 1. For example, this region may be coated at a wet-coat weight of 50 grams per square meter of coated surface area. The reagent strip is dried conventionally with an in-line drying system where the nominal air temperature is at 110° C. The rate of processing is nominally 30-38 meters per minute and depends upon the rheology of the reagent.

The materials are processed in continuous reels such that the electrode pattern is orthogonal to the length of the reel, in the case of the substrate 12. Once the substrate 12 has been coated with reagent, the spacers 16 are slit and placed in a reel-to-reel process onto the substrate 12. Two spacers 16 formed from 100 μm polyester (for example, Melinex 329 available from DuPont) coated with 25 μm PSA (hydrophobic adhesive) on both the dorsal and ventral surfaces are applied to the bottom substrate 12, such that the spacers 16 are separated by 1.5 mm and the working, counter and dose sufficiency electrodes are centered in this gap. A top foil layer 18 formed from 100 μm polyester coated with a hydrophilic film on its ventral surface (using the process described in U.S. Pat. No. 5,997,817) is placed over the spacers 16. The hydrophilic film is coated with a mixture of Vitel and Rhodapex surfactant at a nominal thickness of 10 microns. The top foil layer 18 is laminated using a reel-to-reel process. The test strips can then be produced from the resulting reels of material by means of slitting and cutting.

Although the basic test strip 10 illustrated in FIG. 1 can provide accurate measurements of blood glucose in a whole blood sample, it does not provide any means for the test meter into which it is inserted to identify anything about the test strip. The present invention presents several systems by which information relating to the test strip can be coded directly onto the test strip itself, such that this information can be conveyed to a test meter into which the test strip is inserted.

Figure 2:
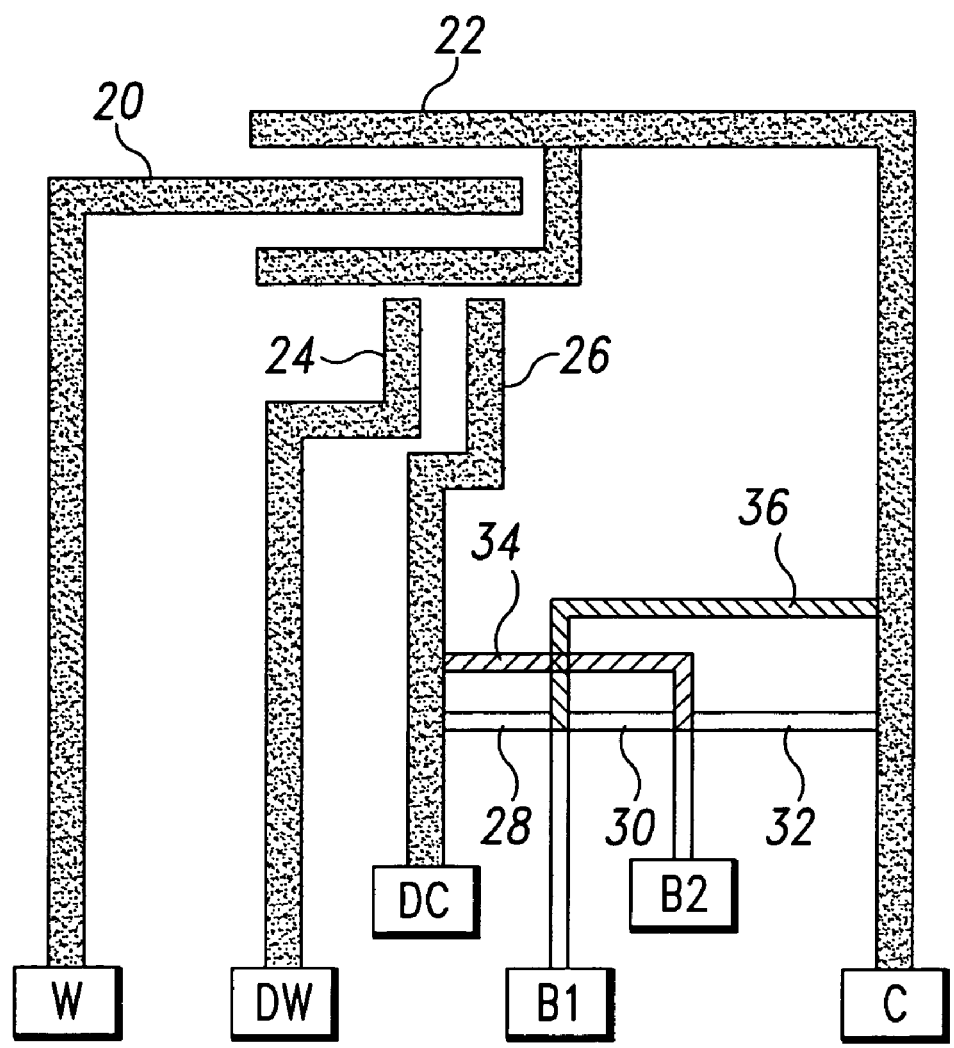
FIG. 2 is a schematic plan view of a first embodiment test strip electrode and contact pad arrangement according to the present invention.

In a first embodiment of the present invention, information about the test strip can be coded directly onto the test strip by the addition of two or more contact pads dedicated to reading such coded information. As illustrated in FIG. 2, a pair of additional information contact pads B1 and B2 are added to the proximal end of the test strip. Additionally, potential conductive links between the information contact pads B1 and B2 and between them and measurement contact pads connected to test strip measurement electrodes are identified at 28, 30, 32, 34 and 36. These links are denominated as potential conductive links because they may either be present or absent in the finished test strip, depending upon the information that is to be coded onto the test strip. Therefore, a "potential conductive link" indicates a conductive link that is found on some, but not all, of a group of otherwise substantially identical test strips. As used herein, the phrase "information contact pad" is defined as a contact pad on the test strip that is either not conductively coupled to a measurement electrode of the test strip at all, or is so coupled only by a potential conductive link. As used herein, the phrase "measurement contact pad" is defined as a contact pad on the test strip that is always conductively coupled to a measurement electrode of the test strip, regardless of the presence or absence of the potential conductive links.

Specifically, potential conductive link 28 couples the DC contact pad and the B1 contact pad. Potential conductive link 30 couples the B1 contact pad and the B2 contact pad. Potential conductive link 32 couples the B2 contact pad and the C contact pad. Potential conductive link 34 couples the DC contact pad and the B2 contact pad. Potential conductive link 36 couples the B1 contact pad and the C contact pad. It should be noted that the first embodiment of the present invention illustrates potential conductive links between the information contact pads B1 and B2 and the measurement contact pads DC and C by way of example only, and that the information contact pads may be conductively linked to any desired measurement contact pad(s) on the test strip.

FIG. 3 illustrates a table showing the possible combinations for the potential conductive links 28-36 formed on any one test strip of the first embodiment. The first five columns of the table represent each of the potential conductive links 28-36, which are labeled C1-C5, respectively. Each of the nine rows of the table numbered 0-8 represent a different number that can be encoded using the potential conductive links 28-36. A "0" in a table position indicates that the potential conductive link is not formed when encoding the number of that row, while a "1" in a table position indicates that the potential conductive link is formed when encoding the number of that row. Note that there are some combinations of potential conductive links that are not allowed because the DC contact pad and the C contact pad cannot be conductively linked without harming the measurement functionality of the test strip measurement electrodes. For example, potential conductive links 34 and 36 may not be used at the same time, as they cross one another and therefore would conductively connect the DC contact pad to the C contact pad. Similarly, potential conductive links 28, 30 and 32 may not be used at the same time.

The last two columns of the table of FIG. 3 are labeled B1 and B2, respectively, and indicate to which of the other contact pads the labeled contact pad is coupled when the number of that row is encoded onto the test strip. For example, when the number six (6) is encoded onto the test strip (i.e. potential conductive links 28 and 32 are formed on the test strip) the B1 contact pad is conductively coupled to the DC contact pad, and the B2 contact pad is conductively coupled to the C contact pad, but B1 and B2 are not conductively coupled to any other contact pads (including to each other). Therefore, a measurement by the test meter of the resistance (either directly or indirectly) between each of the contact pads DC, B1, B2 and C will indicate which of the eight (8) possible numbers has been encoded onto the test strip. The present invention also comprehend other methods for determining the presence or absence of potential conductive links on the test strip other than by measurement of resistance or conductivity. By way of non-limiting example, the potential conductive links can also be sensed in a non-contact fashion by inducing and sensing eddy currents using an electromagnetic field, by capacitive means, by optical scanning techniques, or by other methods that would be apparent to one having ordinary skill in the art.

Note that the absence of all of the potential conductive links 28-36 is preferably not considered to be a valid state as this could be caused by a localized defect obliterating the region of the test strip containing the potential conductive links 28-36, but this state could be considered a valid state in other, non-preferred, embodiments. It should also be noted that a reading of conduction between combinations of contact pads not indicated as a valid combination in the table of FIG. 3 will be interpreted by the test meter as a defective strip with an unintended short.

It will be appreciated that the use of measurement contact pads in combination with dedicated information contact pads in the present invention, and the opportunity to potentially couple each information contact pad to more than one measurement contact pad significantly increases the amount of numbers that may be encoded onto the test strip. By way of comparison, the two (2) information contact pads of the first embodiment of the present invention conservatively allow the coding of eight (8) numbers. The design disclosed in JP 2000352034 would only allow two (2) possible states with two information contact pads, while the design disclosed in EP 1152239A1 would only allow four (4) possible states with two information contact pads.

One method of preparing a test strip encoded with information as described herein is by the use of laser ablation techniques. Examples of the use of these techniques in preparing electrodes for biosensors are described in U.S. patent application Ser. No. 09/866,030, "Biosensors with Laser Ablation Electrodes with a Continuous Coverlay Channel" filed May 25, 2001, and in U.S. patent application Ser. No. 09/411,940, entitled "Laser Defined Features for Patterned Laminates and Electrode," filed Oct. 4, 1999, both disclosures incorporated herein by reference.

It is desirable in the present invention to provide for the accurate placement of the electrical components relative to one another and to the overall biosensor. In a preferred embodiment, the relative placement of components is achieved, at least in part, by the use of broad field laser ablation that is performed through a mask or other device that has a precise pattern for the electrical components. This allows accurate positioning of adjacent edges, which is further enhanced by the close tolerances for the smoothness of the edges.

Figure 4:
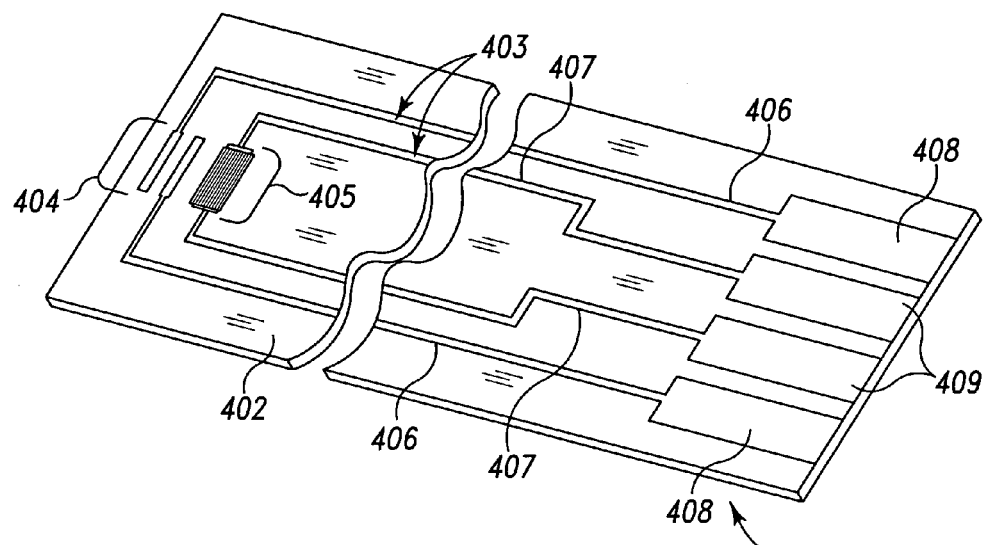
FIG. 4 is a perspective view of a second typical test strip for use in measuring the concentration of an analyte of interest in a biological fluid.

FIG. 4 illustrates a simple biosensor 401 useful for illustrating the laser ablation process of the present invention, including a substrate 402 having formed thereon conductive material 403 defining electrode systems comprising a first electrode set 404 and a second electrode set 405, and corresponding traces 406, 407 and contact pads 408, 409, respectively. The conductive material 403 may contain pure metals or alloys, or other materials, which are metallic conductors. Preferably, the conductive material is absorptive at the wavelength of the laser used to form the electrodes and of a thickness amenable to rapid and precise processing. Non-limiting examples include aluminum, carbon, copper, chromium, gold, indium tin oxide (ITO), palladium, platinum, silver, tin oxide/gold, titanium, mixtures thereof, and alloys or metallic compounds of these elements. Preferably, the conductive material includes noble metals or alloys or their oxides. Most preferably, the conductive material includes gold, palladium, aluminum, titanium, platinum, ITO and chromium. The conductive material ranges in thickness from about 10 nm to 80 nm, more preferably, 30 nm to 70 nm, and most preferably 50 nm. It is appreciated that the thickness of the conductive material depends upon the transmissive property of the material and other factors relating to use of the biosensor.

While not illustrated, it is appreciated that the resulting patterned conductive material can be coated or plated with additional metal layers. For example, the conductive material may be copper, which is then ablated with a laser into an electrode pattern; subsequently, the copper may be plated with a titanium/tungsten layer, and then a gold layer, to form the desired electrodes. Preferably, a single layer of conductive material is used, which lies on the base 402. Although not generally necessary, it is possible to enhance adhesion of the conductive material to the base, as is well known in the art, by using seed or ancillary layers such as chromium nickel or titanium. In preferred embodiments, biosensor 401 has a single layer of gold, palladium, platinum or ITO.

Figure 5:
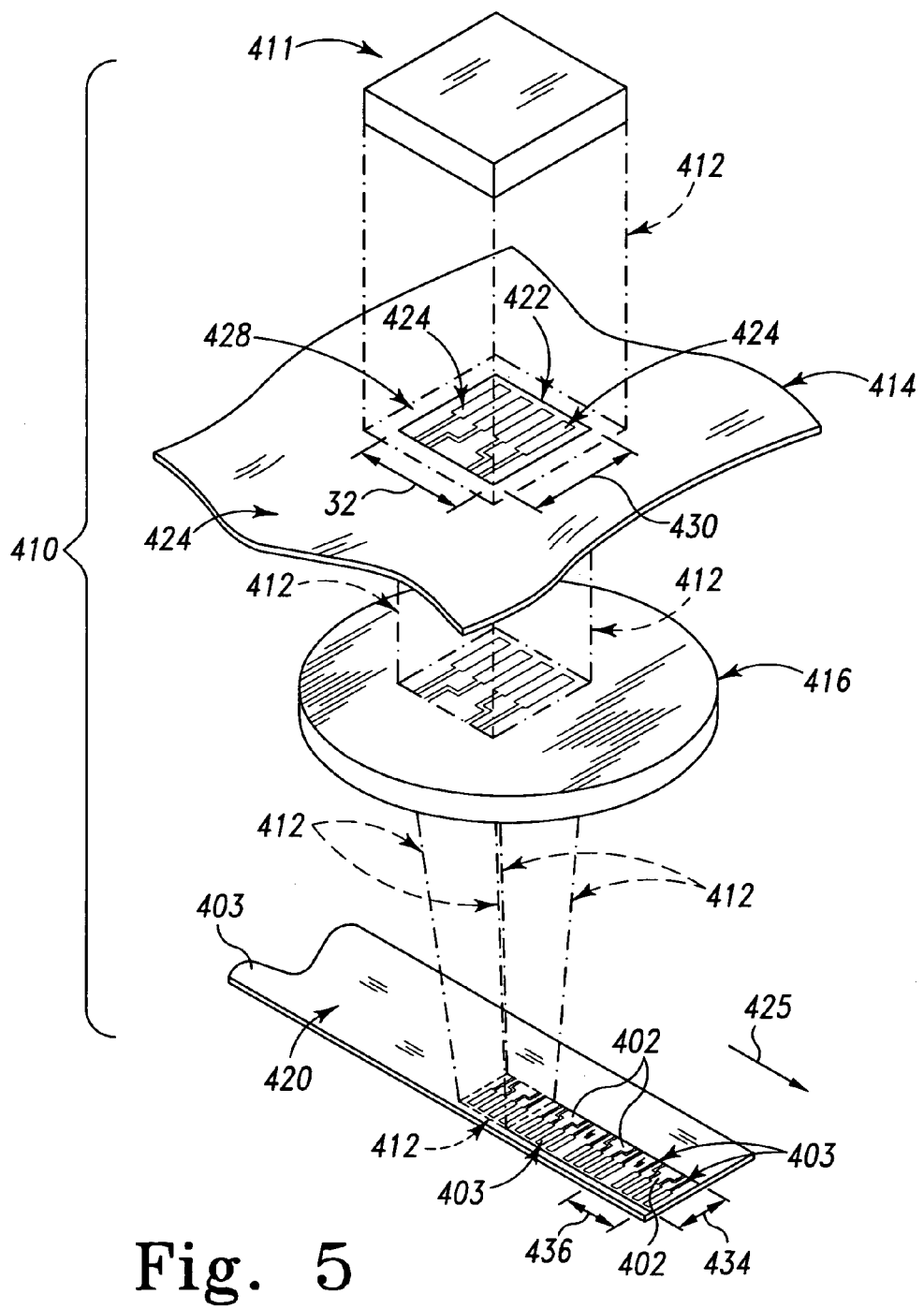
FIG. 5 illustrates a view of an ablation apparatus suitable for use with the present invention.
Figure 6:
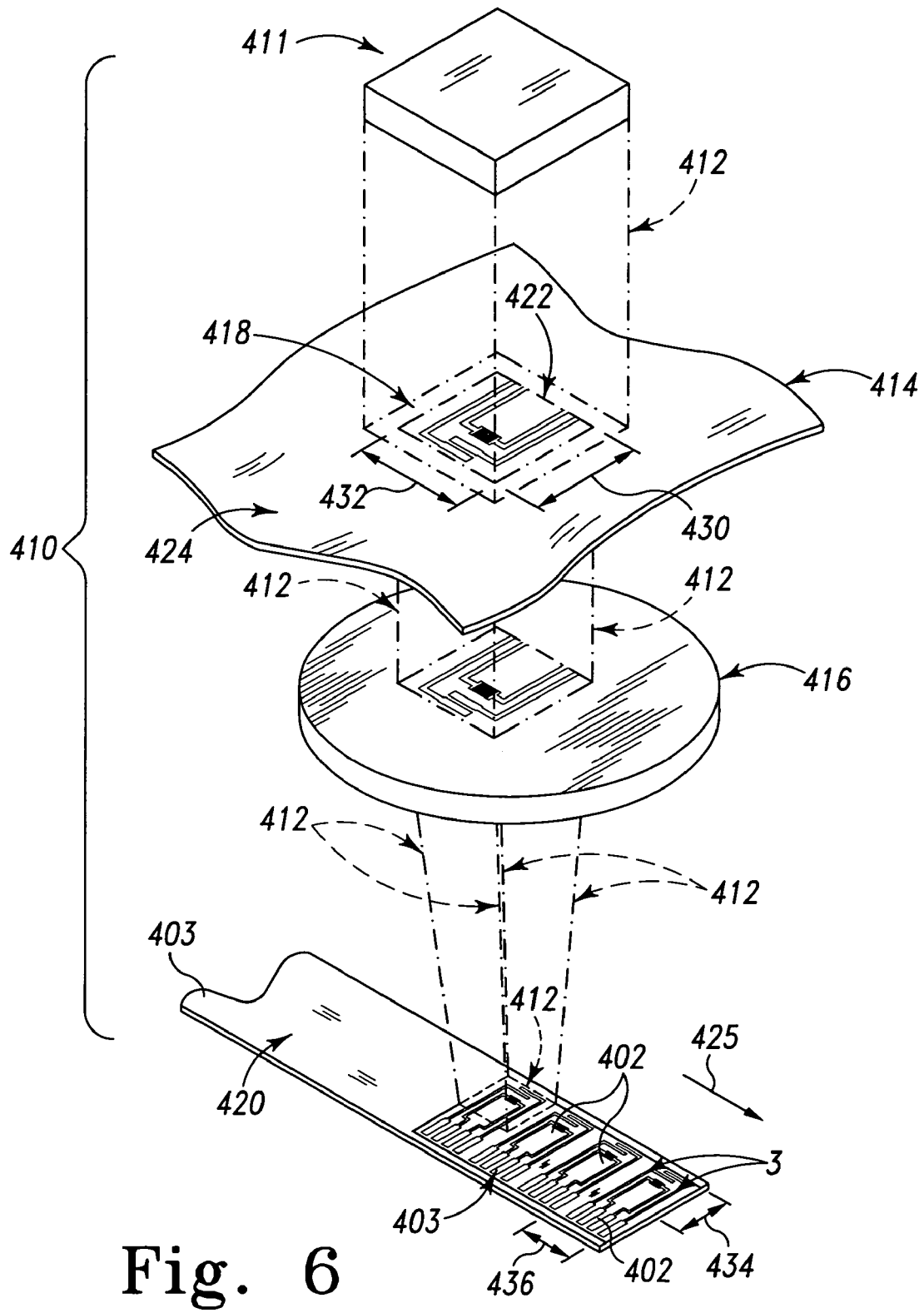
FIG. 6 is a view of the laser ablation apparatus of FIG. 5 showing a second mask.
Figure 7:
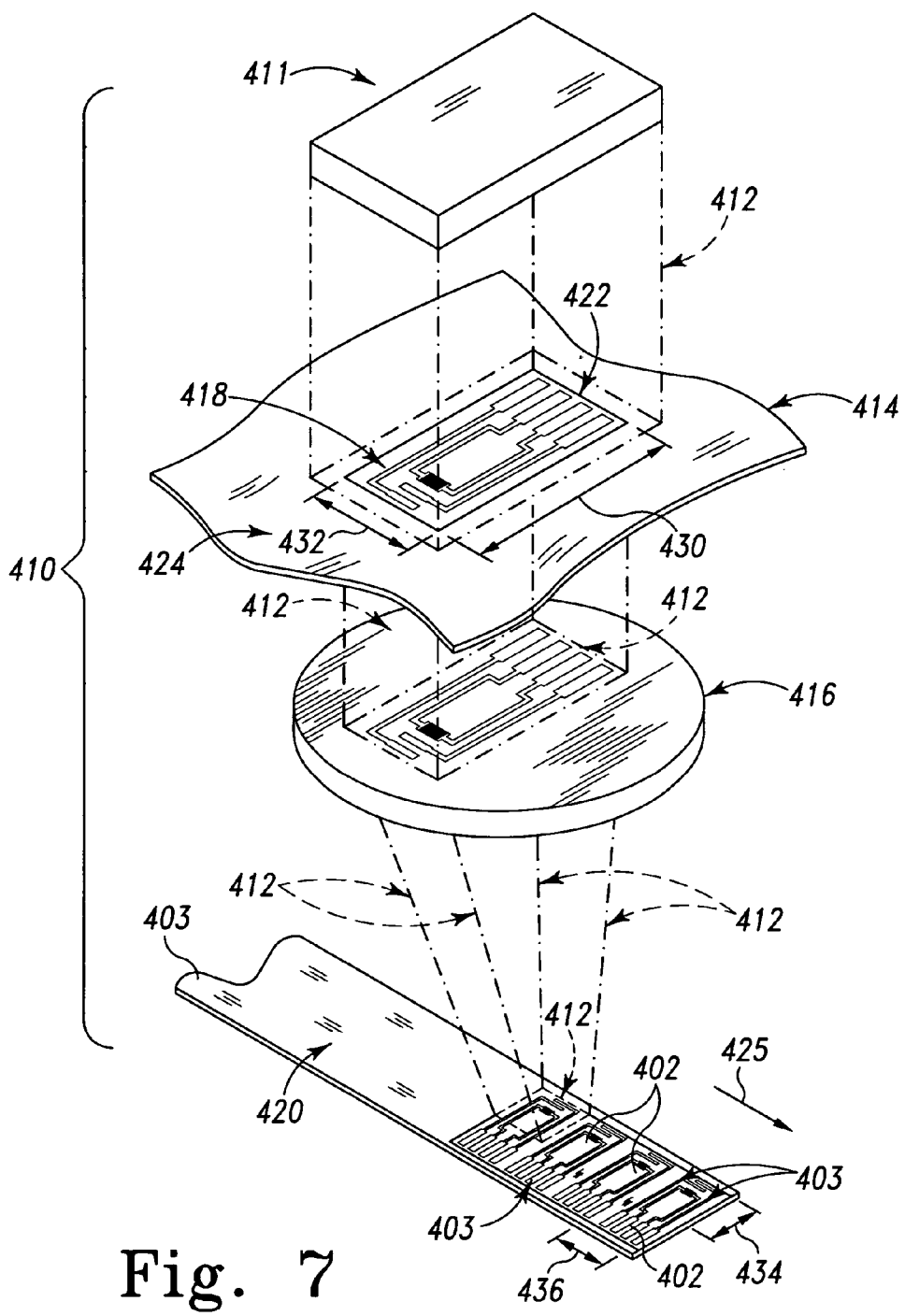
FIG. 7 is a view of an ablation apparatus suitable for use with the present invention.

Biosensor 401 is illustratively manufactured using two apparatuses 10, 10', shown in FIGS. 4, 6 and 7, respectively. It is appreciated that unless otherwise described, the apparatuses 410, 410' operate in a similar manner. Referring first to FIG. 5, biosensor 401 is manufactured by feeding a roll of ribbon 420 having an 80 nm gold laminate, which is about 40 mm in width, into a custom fit broad field laser ablation apparatus 410. The apparatus 410 comprises a laser source 411 producing a beam of laser light 412, a chromium-plated quartz mask 414, and optics 416. It is appreciated that while the illustrated optics 416 is a single lens, optics 416 is preferably a variety of lenses that cooperate to make the light 412 in a pre-determined shape.

A non-limiting example of a suitable ablation apparatus 410 (FIGS. 5-6) is a customized MicrolineLaser 200-4 laser system commercially available from LPKF Laser Electronic GmbH, of Garbsen, Germany, which incorporates an LPX-400, LPX-300 or LPX-200 laser system commercially available from Lambda Physik AG, Göttingen, Germany and a chromium-plated quartz mask commercially available from International Phototool Company, Colorado Springs, Colo.

For the MicrolineLaser 200-4 laser system (FIGS. 5-6), the laser source 411 is a LPX-200 KrF-UV-laser. It is appreciated, however, that higher wavelength UV lasers can be used in accordance with this disclosure. The laser source 411 works at 248 nm, with a pulse energy of 600 mJ, and a pulse repeat frequency of 50 Hz. The intensity of the laser beam 412 can be infinitely adjusted between 3% and 92% by a dielectric beam attenuator (not shown). The beam profile is 27×15 mm² (0.62 sq. inch) and the pulse duration 25 ns. The layout on the mask 414 is homogeneously projected by an optical elements beam expander, homogenizer, and field lens (not shown). The performance of the homogenizer has been determined by measuring the energy profile. The imaging optics 416 transfer the structures of the mask 414 onto the ribbon 420. The imaging ratio is 2:1 to allow a large area to be removed on the one hand, but to keep the energy density below the ablation point of the applied chromium mask on the other hand. While an imaging of 2:1 is illustrated, it is appreciated that the any number of alternative ratios are possible in accordance with this disclosure depending upon the desired design requirements. The ribbon 420 moves as shown by arrow 425 to allow a number of layout segments to be ablated in succession.

The positioning of the mask 414, movement of the ribbon 420, and laser energy are computer controlled. As shown in FIG. 5, the laser beam 412 is projected onto the ribbon 420 to be ablated. Light 412 passing through the clear areas or windows 418 of the mask 414 ablates the metal from the ribbon 420. Chromium coated areas 424 of the mask 414 blocks the laser light 412 and prevent ablation in those areas, resulting in a metallized structure on the ribbon 420 surface. Referring now to FIG. 6, a complete structure of electrical components may require additional ablation steps through a second mask 414'. It is appreciated that depending upon the optics and the size of the electrical component to be ablated, that only a single ablation step or greater than two ablation steps may be necessary in accordance with this disclosure. Further, it is appreciated that instead of multiple masks, that multiple fields may be formed on the same mask in accordance with this disclosure.

Specifically, a second non-limiting example of a suitable ablation apparatus 410' (FIG. 7) is a customized laser system commercially available from LPKF Laser Electronic GmbH, of Garbsen, Germany, which incorporates a Lambda STEEL (Stable energy excimer laser) laser system commercially available from Lambda Physik AG, Göttingen, Germany and a chromium-plated quartz mask commercially available from International Phototool Company, Colorado Springs, Colo. The laser system features up to 1000 mJ pulse energy at a wavelength of 308 nm. Further, the laser system has a frequency of 100 Hz. The apparatus 410' may be formed to produce biosensors with two passes as shown in FIGS. 5 and 6, but preferably its optics permit the formation of a 10×40 mm pattern in a 25 ns single pass.

While not wishing to be bound to a specific theory, it is believed that the laser pulse or beam 412 that passes through the mask 414, 414', 414" is absorbed within less than 1 μm of the surface 402 on the ribbon 420. The photons of the beam 412 have an energy sufficient to cause photo-dissociation and the rapid breaking of chemical bonds at the metal/polymer interface. It is believed that this rapid chemical bond breaking causes a sudden pressure increase within the absorption region and forces material (metal film 403) to be ejected from the polymer base surface. Since typical pulse durations are around 20-25 nanoseconds, the interaction with the material occurs very rapidly and thermal damage to edges of the conductive material 403 and surrounding structures is minimized. The resulting edges of the electrical components have high edge quality and accurate placement as contemplated by the present invention.

Fluence energies used to remove or ablate metals from the ribbon 420 are dependent upon the material from which the ribbon 420 is formed, adhesion of the metal film to the base material, the thickness of the metal film, and possibly the process used to place the film on the base material, i.e. supporting and vapor deposition. Fluence levels for gold on KALADEX® range from about 50 to about 90 mJ/cm², on polyimide about 100 to about 120 mJ/cm², and on MELINEX® about 60 to about 120 mJ/cm². It is understood that fluence levels less than or greater than the above mentioned can be appropriate for other base materials in accordance with the disclosure.

Patterning of areas of the ribbon 420 is achieved by using the masks 414, 414'. Each mask 414, 414' illustratively includes a mask field 422 containing a precise two-dimensional illustration of a pre-determined portion of the electrode component patterns to be formed. FIG. 5 illustrates the mask field 422 including contact pads and a portion of traces. As shown in FIG. 6, the second mask 414' contains a second corresponding portion of the traces and the electrode patterns containing fingers. As previously described, it is appreciated that depending upon the size of the area to be ablated, the mask 414 can contain a complete illustration of the electrode patterns (FIG. 7), or portions of patterns different from those illustrated in FIGS. 5 and 6 in accordance with this disclosure. Preferably, it is contemplated that in one aspect of the present invention, the entire pattern of the electrical components on the test strip are laser ablated at one time, i.e., the broad field encompasses the entire size of the test strip (FIG. 7). In the alternative, and as illustrated in FIGS. 5 and 6, portions of the entire biosensor are done successively.

While mask 414 will be discussed hereafter, it is appreciated that unless indicated otherwise, the discussion will apply to masks 414', 414" as well. Referring to FIG. 5, areas 424 of the mask field 422 protected by the chrome will block the projection of the laser beam 412 to the ribbon 420. Clear areas or windows 418 in the mask field 422 allow the laser beam 412 to pass through the mask 414 and to impact predetermined areas of the ribbon 420. As shown in FIG. 5, the clear area 418 of the mask field 422 corresponds to the areas of the ribbon 420 from which the conductive material 403 is to be removed.

Further, the mask field 422 has a length shown by line 430 and a width as shown by line 432. Given the imaging ratio of 2:1 of the LPX-200, it is appreciated that the length 30 of the mask is two times the length of a length 434 of the resulting pattern and the width 432 of the mask is two times the width of a width 436 of the resulting pattern on ribbon 420. The optics 416 reduces the size of laser beam 412 that strikes the ribbon 420. It is appreciated that the relative dimensions of the mask field 422 and the resulting pattern can vary in accordance with this disclosure. Mask 414' (FIG. 6) is used to complete the two-dimensional illustration of the electrical components.

Continuing to refer to FIG. 5, in the laser ablation apparatus 410 the excimer laser source 411 emits beam 412, which passes through the chrome-on-quartz mask 414. The mask field 422 causes parts of the laser beam 412 to be reflected while allowing other parts of the beam to pass through, creating a pattern on the gold film where impacted by the laser beam 412. It is appreciated that ribbon 420 can be stationary relative to apparatus 410 or move continuously on a roll through apparatus 410. Accordingly, non-limiting rates of movement of the ribbon 420 can be from about 0 m/min to about 100 m/min, more preferably about 30 m/min to about 60 m/min. It is appreciated that the rate of movement of the ribbon 420 is limited only by the apparatus 410 selected and may well exceed 100 m/min depending upon the pulse duration of the laser source 411 in accordance with the present disclosure.

Once the pattern of the mask 414 is created on the ribbon 420, the ribbon is rewound and fed through the apparatus 410 again, with mask 414' (FIG. 6). It is appreciated, that alternatively, laser apparatus 410 could be positioned in series in accordance with this disclosure. Thus, by using masks 414, 414', large areas of the ribbon 420 can be patterned using step-and-repeat processes involving multiple mask fields 422 in the same mask area to enable the economical creation of intricate electrode patterns and other electrical components on a substrate of the base, the precise edges of the electrode components, and the removal of greater amounts of the metallic film from the base material.

The ability to code information directly onto the test strip can dramatically increase the capabilities of the test strip and enhance its interaction with the test meter. For example, it is well known in the art to supply the test meter with calibration data applicable to any given manufacturing lot of test strips. Typically, this is done by supplying a read-only memory key (ROM key) with each vial of test strips, where the ROM key has encoded thereon the calibration data applicable to the test strips in the vial. Before using the test strips from the vial, the user inserts the ROM key into a port in the test meter so that the test meter may have access to this data while performing tests using the test strip. The quality of the measurement result can be verified by allowing the meter to electronically assess the applicability of the ROM key data to the test strip currently inserted into the meter, without the need for an optical reader to read bar code information on the test strip as has been taught in the prior art.

Figure 8:
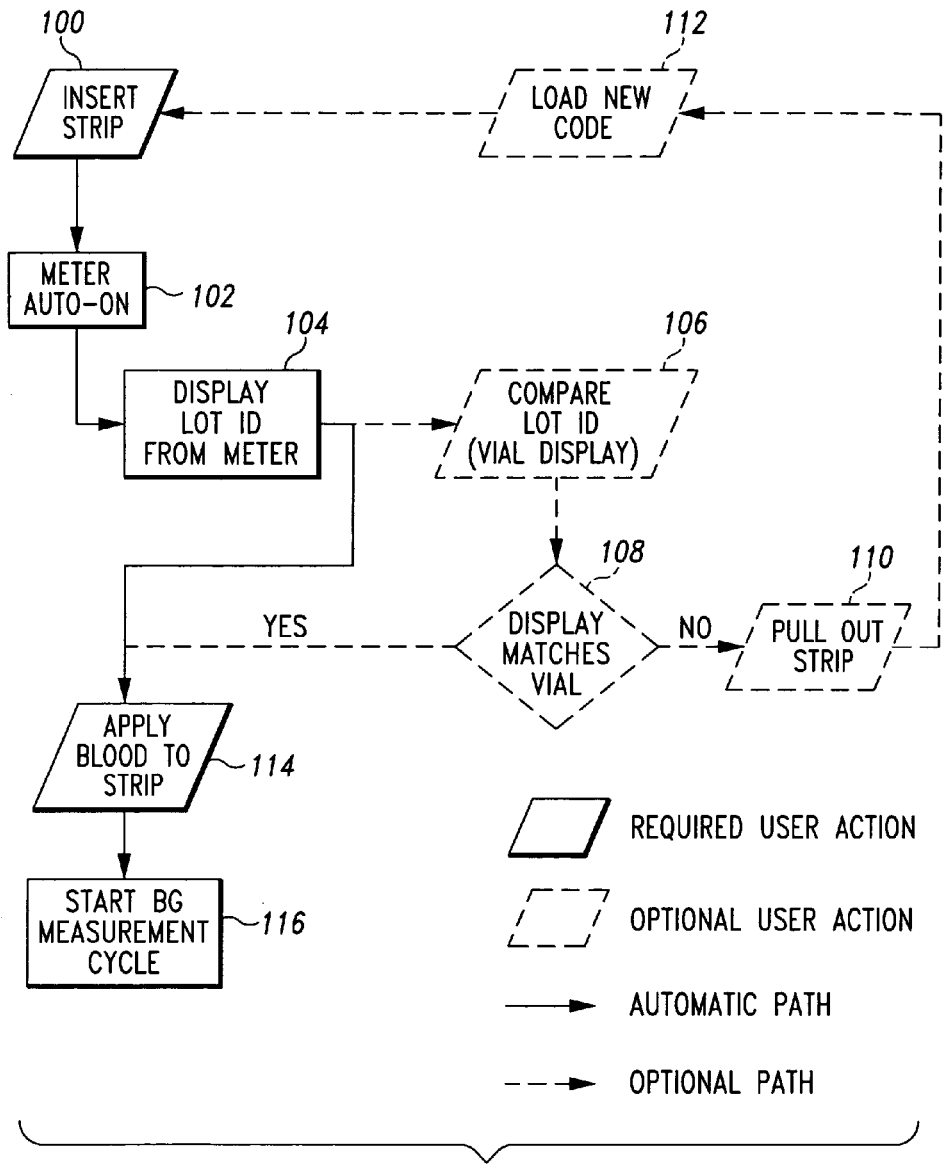
FIG. 8 is a schematic process flow diagram of a prior art process for verifying the applicability of the calibration data in the test meter to the test strip currently inserted into the test meter.

Current commercially-available products require the user to be involved in verifying the correct ROM key has been inserted into the test meter for the test strip currently being used. For example, FIG. 8 illustrates a typical prior art process for verifying the match between the ROM key data and the test strip lot identification (ID) number. Prior to executing this process, the ROM key has been inserted into the test meter, the ROM data has been loaded into the test meter, and the test meter is turned off. The process begins by inserting a test strip (step 100) into the test meter, which causes the test meter to automatically turn on (step 102). The test meter displays the lot ID of the currently loaded calibration data (step 104) in order to give the user the chance to verify that this lot ID matches the lot ID printed on the vial/package (for example) containing a plurality of test strips from the same production lot as the test strip currently inserted into the test meter.

Because the process relies upon the user to perform this check, there is no way to guarantee that it is done or if it is, that it is done accurately. The process of FIG. 8 therefore indicates an optional step for the user to compare the lot ID on the test meter display to the lot ID on the test strip vial (step 106) and to determine (step 108) if there is a match. If the two lot IDs do not match, then the user should remove the test strip (step 110) and insert the ROM key that matches the test strip vial into the test meter (step 112) so that the proper calibration code can be loaded into the test meter. The process would then start over at step 100 with the insertion of the test strip. Once it has been determined that the test meter's calibration code lot ID matches the lot ID of the test strip (step 108), then the measurement sequence can continue by applying blood to the test strip (step 114) and beginning the blood glucose measurement cycle (step 116).

It will be appreciated that responsibility for verification of the accuracy of the measurement calibration data has been placed completely in the hands of the user in the prior art process of FIG. 8. It is sometimes encountered that users ignore stated use instructions provided with the test strips. One such example is the removal of test strips from a first vial that were manufactured in lot X and consolidating these test strips into a second vial containing test strips manufactured in lot Y. Therefore, it is desirable to bring lot specific calibration information to the individual test strip level instead of to the vial level as is done in the prior art.

Figure 9:
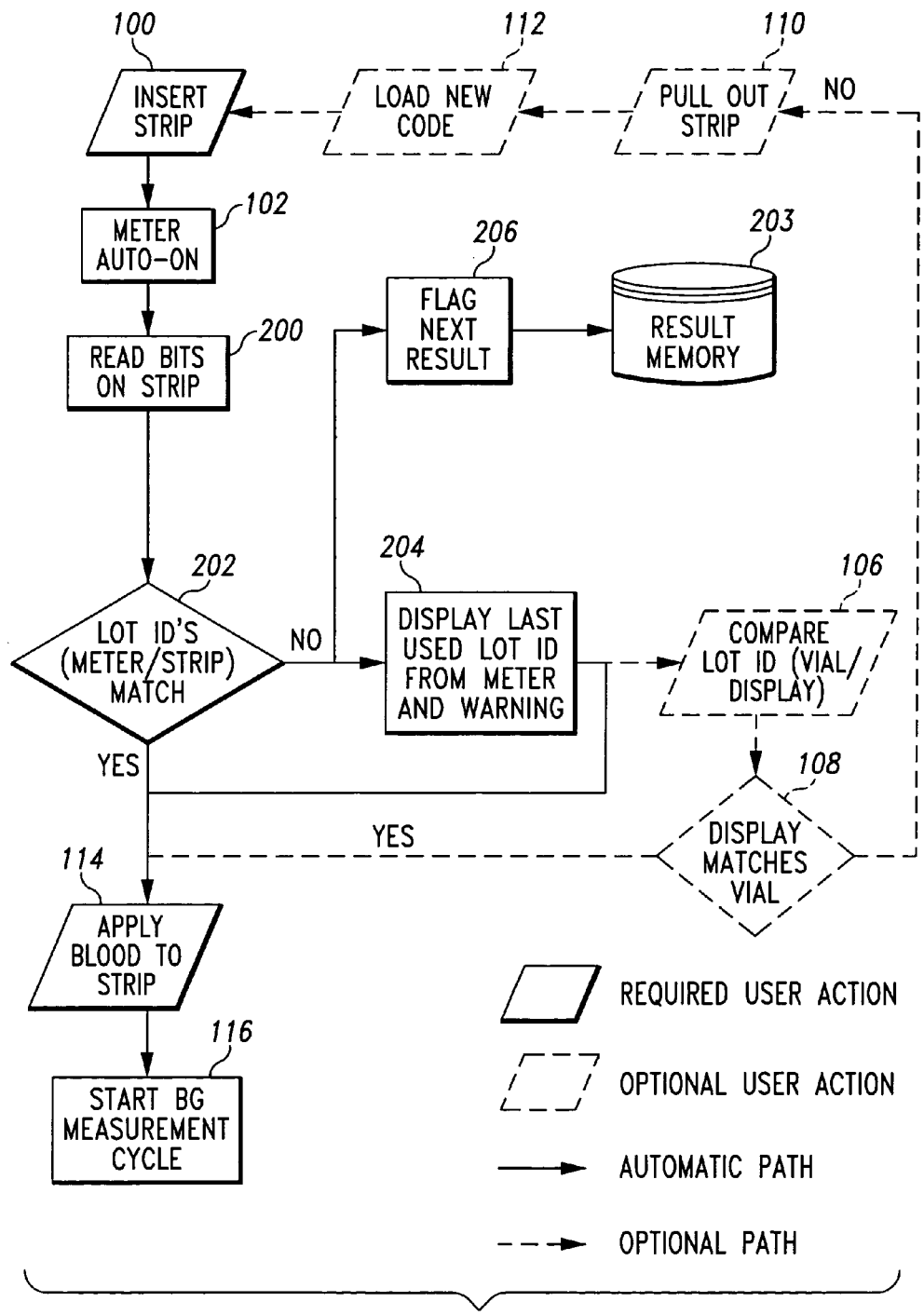
FIG. 9 is a schematic process flow diagram of a first embodiment process of the present invention for verifying the applicability of the calibration data in the test meter to the test strip currently inserted into the test meter.

In order to remove the possibility of human error or neglect from the process, and to thereby improve the quality of the measurement, the information contact pads of the present invention allow the test meter itself to perform checks as to the applicability of the currently loaded calibration data to the currently inserted test strip. A first embodiment process of the present invention to allow the test meter to actively participate in such verification is illustrated in FIG. 9. The steps of the process of FIG. 9 that are identical to the corresponding steps in FIG. 8 are numbered with the same reference designators.

Prior to executing this process, the ROM key has been inserted into the test meter, the ROM data has been loaded into the test meter, and the test meter is turned off. The process begins by inserting a test strip (step 100) into the test meter, which causes the test meter to automatically turn on (step 102). The test meter then measures the conductivity between the various information and measurement contact pads on the test strip that have been designated for encoding information onto the test strip in order to ascertain the lot or family ID of the test strip (step 200). Depending upon the quantity of information that may be encoded onto the test strip, it may or may not be possible to code a unique production lot number onto the test strip. If there is not sufficient space for unique production lot IDs to be encoded, it is still possible to encoded calibration family information onto the test strip. For example, the test strips usable in the test meter may be of two or more families where significant differences exist between the family test strip designs. For example, two families may use a different reagent on the test strip. In such situations, the test meter can still verify that the loaded calibration data matches the test strip family encoded onto the test strip, even if it is not possible to verify the precise production lot of the test strip. Therefore, as used herein, the phrase "lot ID" is intended to encompass any information that identifies a group to which the test strip or calibration data belongs, even if that group is not as small as a production lot of the test strip.

Returning to the process of FIG. 9, the test meter compares (step 202) the lot ID of the calibration data stored within the ROM key currently inserted into the meter (or calibration data previously-loaded into the test meter internal memory) to the lot ID read from the test strip. If they do not match, the test meter displays the lot ID of the currently loaded calibration data (step 204) and a warning in order to give the user the chance to insert a correct test strip or to insert a different ROM key into the test meter. Alternatively, the test meter may simply display an error message to the user. The fact that the lot IDs do not match is flagged (step 206) in the test meter's result memory 208 so that there is a record in the memory 208 that the measurement result obtained is suspect in view of the discrepancy in the lot IDs. Alternatively, the user may be prohibited from running a test and the process may be aborted.

Because in some embodiments it is desired that the test meter not be completely disabled if the lot IDs do not match, the process of FIG. 9 indicates an optional step for the user to compare the lot ID on the test meter display to the lot ID on the test strip vial (step 106) and to determine (step 108) if there is a match. If the two lot IDs do not match, then the user should remove the test strip (step 110) and insert the ROM key that matches the test strip vial into the test meter (step 112) so that the proper calibration code can be loaded into the test meter. The process would then start over at step 100 with the insertion of the test strip.

Also optionally, if the test meter has the capacity to store more than one calibration dataset within the meter's internal memory, then the meter may determine the multiple lot IDs of calibration data that may be stored within the test meter and automatically choose the calibration dataset that matches the test strip currently inserted into the meter. The meter can then return to step 114.

Once it has been determined that the test meter's calibration code lot ID matches the lot ID of the test strip (step 108), then the measurement sequence can continue by applying blood to the test strip (step 114) and beginning the blood glucose measurement cycle (step 116). It will be appreciated that the process of FIG. 9 represents an improvement over the prior art process of FIG. 8 in that the user is automatically warned when the lot ID of the test strip does not match the lot ID of the currently-selected calibration dataset. Furthermore, if a test is conducted with this mismatched combination, then the result memory within the test meter is flagged to indicate that the result may not be as accurate as would be the case if the correct calibration dataset were used.

As a further example of the usefulness of encoding information directly onto the test strip, the present invention allows the test strip to activate or deactivate certain features programmed into the test meter. For example, a single test meter may be designed to be used in several different geographic markets, where a different language is spoken in each market. By encoding the test strips with information indicating in which market the test strips were sold, the encoded information can cause the test meter to display user instructions and data in a language that is appropriate for that market. Also, a meter may be designed for sale in a certain geographic market and it is desired that the meter not be used with test strips obtained in a different geographic market (for example when governmental regulations require the test strips sold in one geographic market to have different features than those sold in other geographic markets). In this situation, information coded onto the test strip may be used by the test meter to determine that the test strip did not originate in the designated geographic market and therefore may not provide the features required by regulation, in which case the test may be aborted or flagged.

Further, a business model (subscription business model) may be applied for the distribution of test strips where proliferation of the test strips into other sales channels is not desired. For example, users may enroll into a subscription program in which they are provided with a test meter designed for use by subscription participants, and the subscription participants may be provided with subscription test strips on a regular basis (for example by mail or any other convenient form of delivery). Using the techniques of the present invention, the "subscription test strips" may be encoded to indicate that they were supplied to a subscription participant. For a variety of reasons, the manufacturer of the subscription test strips may not want the subscription test strips to be sold in other channels of trade. One way to prevent this is to design test meters provided to users who are not subscription participants that will not work with subscription test strips. Therefore, the present invention may be used to provide test meters to subscription participants in the subscription business model that are programmed to accept subscription test strips encoded to indicate that they are delivered to a user on the basis of a subscription, while other test meters are programmed not to accept subscription test strips so encoded.

As a further example, the test meter can have certain functionalities (software- and/or hardware-implemented) designed into the meter that are not active when the test meter is first sold. The performance of the test meter can then be upgraded at a later date by including information encoded on the test strips sold at that later time that will be recognized by the meter as an instruction to activate these latent features. As used herein, the phrase "activating a latent feature of the test meter" comprehends turning on a test meter functionality that previously was not active, such that the test meter functionality thereafter remains activated indefinitely (i.e. after the current test with the present test strip is finished).

Another example of information that can be encoded onto the test strip using the present invention is an indication of whether the test strip was sold to the hospital market or to the consumer market. Having this information may allow the test meter to take action accordingly, such as displaying user instructions in less detail for the hospital professional. It will be appreciated by those skilled in the art that a variety of types of communication between the test strip and the test meter may be facilitated by the information encoding provided by the present invention.

Figure 10:
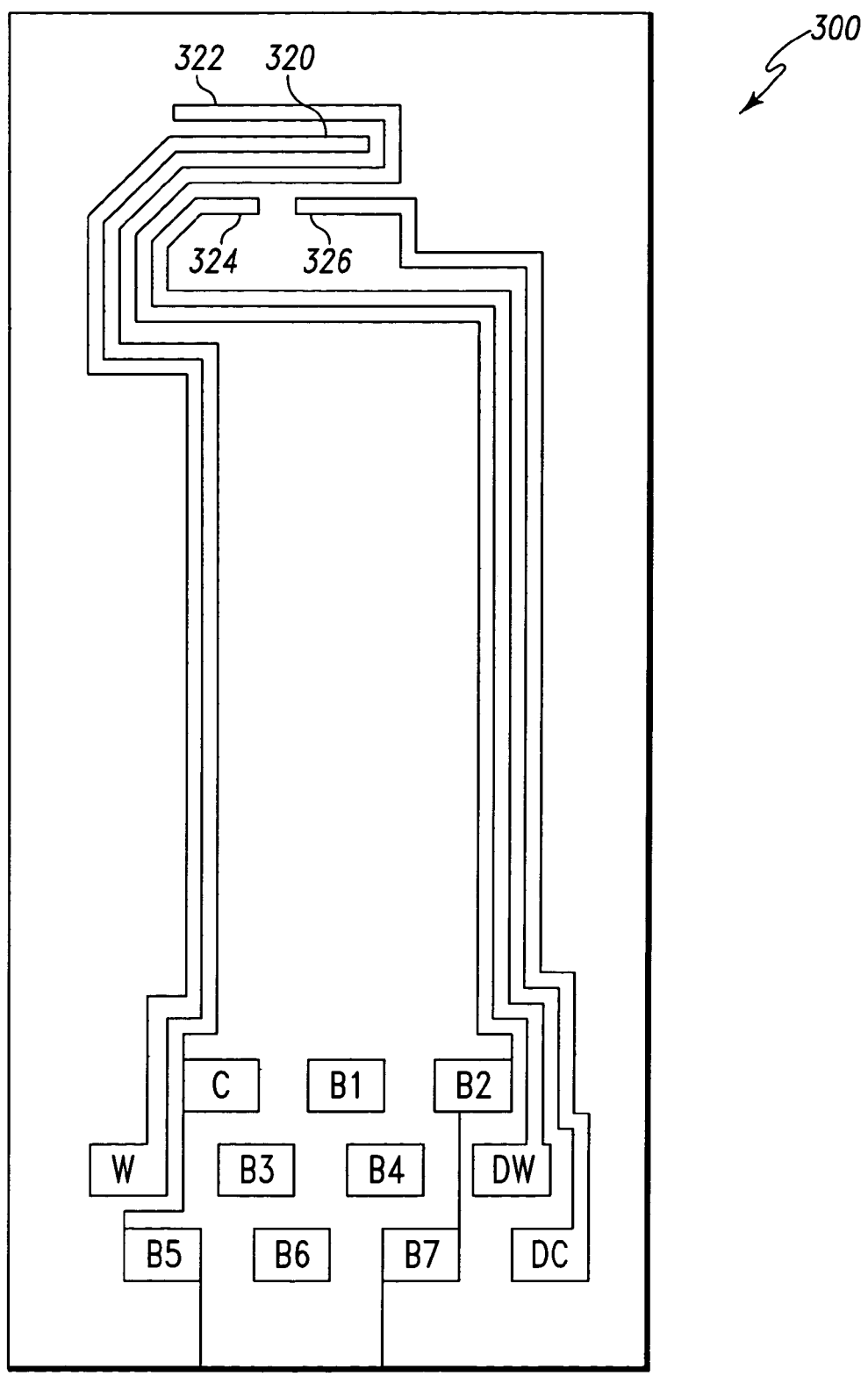
FIG. 10 is a schematic plan view of a second embodiment test strip electrode and contact pad arrangement according to the present invention.

A second embodiment test strip configuration that allows information to be encoded directly onto the test strip is illustrated in FIG. 10 and indicated generally at 300. The test strip 300 may preferably be formed generally as described above with respect to the test strips 10 and 401, with working 320, counter 322, dose sufficiency working 324, and dose sufficiency counter 326 electrodes may be formed as shown and coupled, respectively, to measurement contact pads W, C, DW and DC. These contact pads provide a conductive area upon the test strip 300 to be contacted by an electrical connector contact of the test meter once the test strip 300 is inserted into the test meter. The test strip may be formed with a sample inlet in the distal end of the test strip (as shown in FIG. 10), or with a sample inlet on the side of the test strip as shown in FIG. 1. The functionality of the information encoding portion thereof is not affected by the positioning of the measurement electrodes in either position.

It will be noted from an examination of FIG. 10 that the area surrounding the counter electrode contact pad C is formed to provide a relatively large expanse of conductive layer, which is divided into information contact pad positions B1-B7. In the second embodiment of the present invention, the conductive layer may be formed during manufacture of the test strip such that the conductive layer is either present or absent within each of the contact pad positions B1-B7, depending upon what number is to be encoded onto the test strip 300. It should be noted that the counter electrode contact pad C is always formed with the conductive layer present in this area, as this contact pad is always necessary for the making of measurements.

Each of the contact pads C, W, DC and DW, as well as each of the contact pad positions B1-B7 are contacted by individual contacts of a multi-pin electrical connector located within the test meter when the test strip 300 is inserted into the test meter. The multi-pin electrical connector allows electrical signals to be applied from the test meter to the test strip and vice versa. The test meter is programmed (by means well-known in the art), to measure the conductivity between the counter electrode contact pad C and each of the contact pad positions B1-B7. The contact pad C can therefore be selectively conductively coupled to each of the contact pad positions B1-B7 depending upon whether the conductive layer is formed, respectively, in each of the contact pad positions B1-B7. By measuring the conductivity between the contact pad C and each of the contact pad positions B1-B7, the test meter is able to determine the presence or absence of the conductive layer in each of the contact pad positions B1-B7. By assigning, for example, a digital value of "1" when the conductive layer is present in a particular contact pad position and a digital value of "0" when the conductive layer is absent in a particular contact pad position, a digital word may be encoded onto the test strip 300.

It will be appreciated that all of the desirable benefits discussed hereinabove with respect to the first embodiment of the present invention may also be achieved using the second embodiment of the present invention. The second embodiment has the added advantage that, because the contact pad positions B1-B7 can never be conductively coupled to more than one measurement electrode, there are no "forbidden" states and each of the contact pad positions B1-B7 may be coded as a "0" or "1" in any possible seven digit digital word to be encoded onto the test strip. This provides $2^7$ or 128 possible unique words that can be encoded onto the test strip using the contact pad positions B1-B7. The number of contact pad positions that can be designated for such information encoding is only limited by the available space on the test strip surface, the resolution of the process used to define the conductive features on the test strip, the electrical connector contact spacing, and the tolerance stack-ups relevant to placing the connector contact on the contact pad position once the test strip is inserted into the test meter.

Furthermore, the number of possible states in the second embodiment of the present invention can be further increased by severing the conductive path between individual pairs of the contact pad positions B1-B7. Therefore, a connector contacting contact pad B1 (for example) can check for electrical continuity not only with contact pad C (as described hereinabove), but also for electrical continuity with any of the other contact pads B2-B7.

Figure 11:
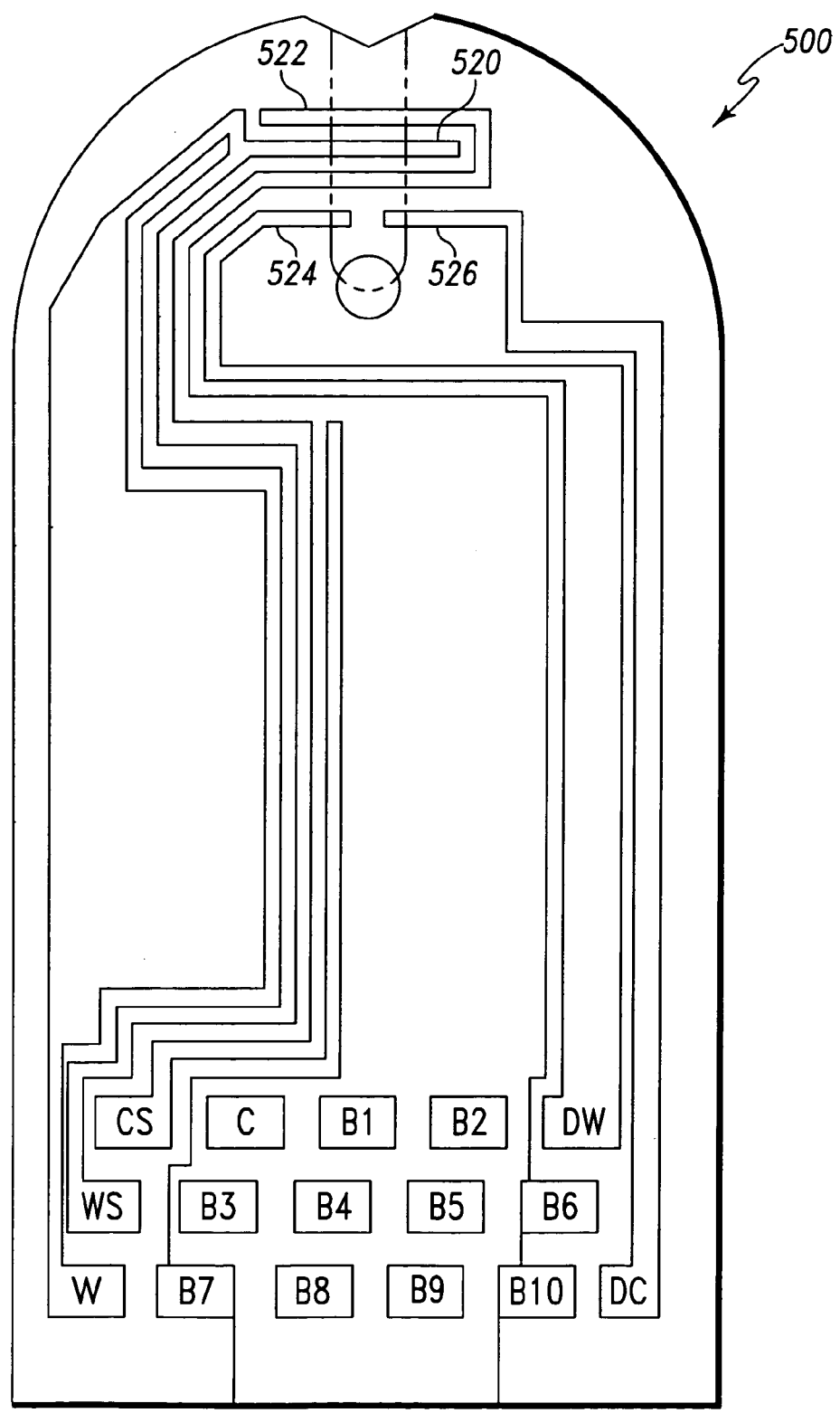
FIG. 11 is a schematic plan view of a third embodiment test strip electrode and contact pad arrangement according to the present invention.

The laser ablation process described hereinabove allows for resolution of test strip conductive features not previously achievable using prior art techniques such as screen printing and photolithography. Because of this, relatively large quantities of data can be coded onto the test strip when the conductive features are formed using the laser ablation process. For example, a third embodiment of the present invention is illustrated in FIG. 11 and indicated generally at 500. The test strip 500 is similar to the test strip 300 of FIG. 10, except that the resolution of the laser ablation process allows for an even greater number of contact pads to be formed on the test strip. Equivalent structures in FIG. 11 are given the same reference designators as used in FIG. 10. A total of sixteen contact pads are formed on the test strip 500, with B1-B10 being designated as information contact pads in addition to the measurement contact pads W, WS, C, CS, DW and DC coupled to working 520, counter 522, dose sufficiency working 524, and dose sufficiency counter 526 electrodes. These contact pads provide a conductive area upon the test strip 500 to be contacted by an electrical connector contact of the test meter once the test strip 500 is inserted into the test meter. The test strip may be formed with a sample inlet in the distal end of the test strip (as shown in FIG. 11), or with a sample inlet on the side of the test strip as shown in FIG. 1. The functionality of the information encoding portion thereof is not affected by the positioning of the measurement electrodes in either position.

As with the second embodiment of FIG. 10, it will be noted from an examination of FIG. 11 that the area surrounding the counter electrode contact pad C is formed to provide a relatively large expanse of conductive layer, which is divided into information contact pad positions B1-B10. In the third embodiment of the present invention, the conductive layer may be formed during manufacture of the test strip such that the conductive layer is either present or absent within each of the contact pad positions B1-B10, depending upon what number is to be encoded onto the test strip 500. As noted hereinabove, the counter electrode contact pad C is always formed with the conductive layer present in this area, as this contact pad is always necessary for the making of measurements.

Each of the contact pads C, CS, W, WS, DC and DW, as well as each of the contact pad positions B1-B10 are contacted by individual contacts of a multi-pin electrical connector located within the test meter when the test strip 500 is inserted into the test meter. The multi-pin electrical connector allows electrical signals to be applied from the test meter to the test strip and vice versa. The test meter is programmed to measure the conductivity between the counter electrode contact pad C and each of the contact pad positions B1-B10. The contact pad C can therefore be selectively conductively coupled to each of the contact pad positions B1-B10 depending upon whether the conductive layer is formed, respectively, in each of the contact pad positions B1-B10. By measuring the conductivity between the contact pad C and each of the contact pad positions B1-B10, the test meter is able to determine the presence or absence of the conductive layer in each of the contact pad positions B1-B10. By assigning, for example, a digital value of "1" when the conductive layer is present in a particular contact pad position and a digital value of "0" when the conductive layer is absent in a particular contact pad position, a digital word may be encoded onto the test strip 500.

It will be appreciated that, as with the second embodiment, all of the desirable benefits discussed hereinabove with respect to the first embodiment of the present invention may also be achieved using the third embodiment of the present invention. Like the second embodiment, the third embodiment has the added advantage that, because the contact pad positions B1-B10 can never be conductively coupled to more than one measurement electrode, there are no "forbidden" states and each of the contact pad positions B1-B10 may be coded as a "0" or "1" in any possible ten digit digital word to be encoded onto the test strip. This provides $2^{10}$ or 1,024 possible unique words that can be encoded onto the test strip using the contact pad positions B1-B10.

Furthermore, as with the second embodiment test strip 300, the number of possible states in the third embodiment test strip 500 of the present invention can be further increased by severing the conductive path between individual pairs of the contact pad positions B1-B10. Therefore, a connector contacting contact pad B1 (for example) can check for electrical continuity not only with contact pad C (as described hereinabove), but also for electrical continuity with any of the other contact pads B2-B10. This greatly increases the number of unique digital words that can be encoded onto the test strip 500.

It should be noted that the contact pad densities achieved in the present invention through the use of the laser ablation process represent a significant advancement over the prior art. For example, published European patent application EP 1 024 358 A1 discloses a system which uses up to 35 contact pads on a single test strip; however, the density of features is so low that the inventors are forced to contact only five of those contact pads at any one time. Not only does this require much more test strip surface area than the present invention to form the same number of contact pads, but it is impossible for the test meter to make conductivity checks between each of the contact pads because the test meter is never in contact with more than five of the contact pads at any one time. The tight control of feature dimensions enabled by the laser ablation process of the present invention allows for the use of contact pad density never before achieved in the art. For example, the embodiment of FIG. 10 allows eleven contact pads to be contacted simultaneously by the test meter connector. Even greater density is achieved in the embodiment of FIG. 11, where sixteen contact pads may be contacted simultaneously by the test meter connector. Some embodiments of the present invention therefore preferably include at least ten test strip contact pads coupled to at least ten test meter connector contacts; more preferably include at least eleven test strip contact pads coupled to at least eleven test meter connector contacts; and most preferably includes at least fifteen test strip contact pads coupled to at least fifteen test meter connector contacts.

Figure 12:
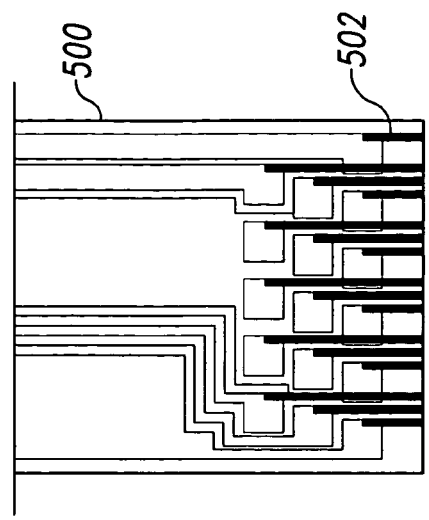
FIG. 12 is a schematic plan view of an electrical connector-to-test strip contact pad interface illustrating worst case left tolerance stack-ups.
Figure 13:
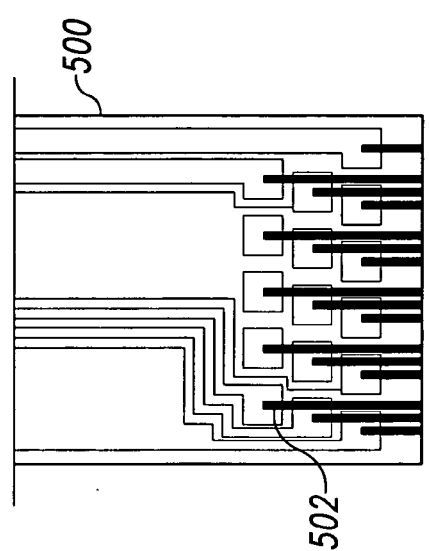
FIG. 13 is a schematic plan view of the electrical connector-to-test strip contact pad interface of FIG. 12 illustrating normal case tolerance stack-ups.
Figure 14:
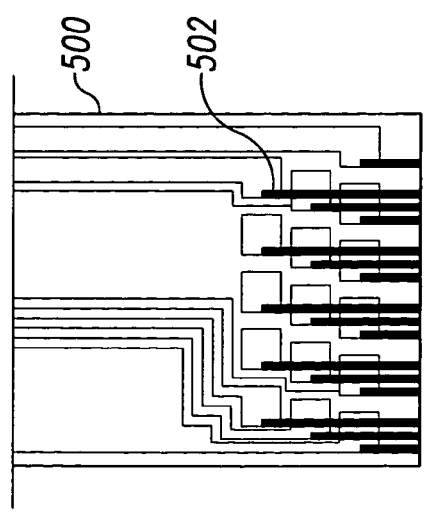
FIG. 14 is a schematic plan view of the electrical connector-to-test strip contact pad interface of FIG. 12 illustrating worst case right tolerance stack-ups.

FIGS. 12-14 illustrate a preferred embodiment multiple-pin electrical connector mating with the third embodiment test strip 500 of FIG. 11. The electrical connector is housed in the test meter (not shown) and includes multiple contacts that produce contact traces 502 when mated with respective contact pads on the test strip 500 when the test strip 500 is inserted into the test meter electrical connector. FIG. 13 illustrates the nominal case in which each electrical connector contact is positioned approximately at the center of the respective test strip 500 contact pad when the test strip 500 is mated to the test meter. In the preferred embodiment, the tolerances of the placement of the conductive features on the test strip 500, as well as the tolerances of the placement of the electrical connector contacts with respect to the test strip mating port of the test meter are controlled such that the worst case tolerance stack-ups will still result in reliable contact between each connector contact and the respective contact pad. As can be seen in FIG. 12, when all of the tolerances are at their maximum so as to move the connector contacts left with respect to their respective contact pads, the electrical contacts are still positioned to make reliable electrical contact with the respective contact pad, and all of the contact pads B1-B10 are still electrically connected to the contact pad C (if their respective metallization is present) even if the mechanical interaction of the connector contacts with the test strip during insertion completely removes the metallization in the areas of contact traces 502. Similarly, as can be seen in FIG. 14, when all of the tolerances are at their maximum so as to move the connector contacts right with respect to their respective contact pads, the electrical contacts are still positioned to make reliable electrical contact with the respective contact pad, and all of the contact pads B1-B10 are still electrically connected to the contact pad C (if their respective metallization is present) even if the mechanical interaction of the connector contacts with the test strip during insertion completely removes the metallization in the areas of contact traces 502.

Figure 15:
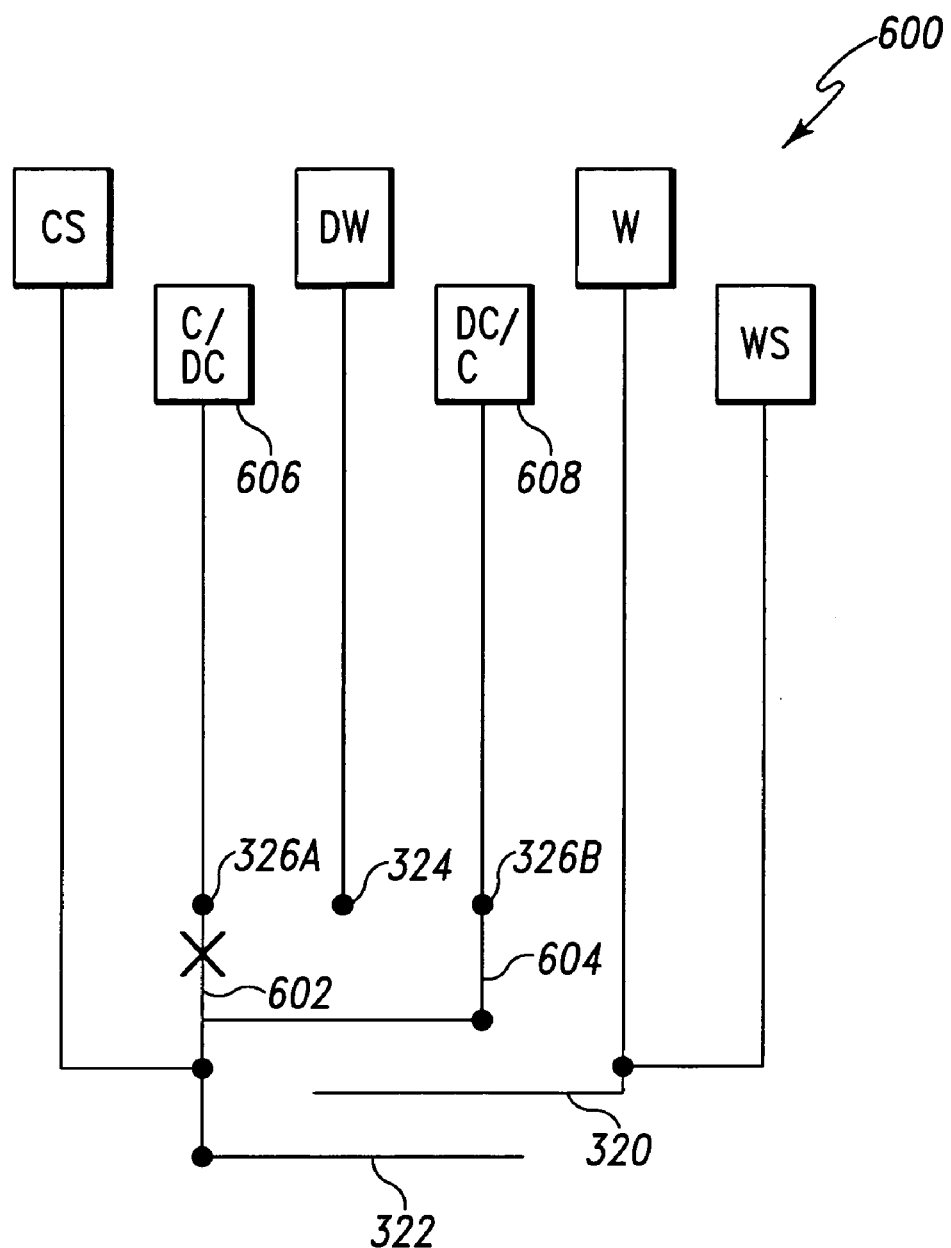
FIG. 15 is a schematic plan view of a fourth embodiment test strip electrode and contact pad arrangement according to the present invention.

A fourth embodiment test strip of the present invention is schematically illustrated in FIG. 15 and designated as 600. The test strip 600 is similar to the test strip 300 of FIG. 10, except that the fourth embodiment uses only six contact pads on the test strip. Embodiments using fewer or more contact pads are contemplated by the present invention. Equivalent structures in FIG. 15 are given the same reference designators as used in FIG. 10. The test strip includes a working electrode 320, a counter electrode 322, a dose sufficiency working electrode 324, and two potential dose sufficiency counter electrodes 326A and 326B. Each of the electrodes is coupled to at least one contact pad formed on the test strip 600.

The working electrode 320 is coupled to both a W and a WS contact pad. The counter electrode 322 is coupled to a C contact pad and a CS contact pad, although which contact pad is designated as C is optional as explained hereinbelow. The dose sufficiency working electrode 324 is coupled to a DW contact pad. The dose sufficiency counter electrode 326A/326B is coupled to a DC contact pad, although which contact pad is designated as DC is optional as explained hereinbelow.

The test strip 600 allows a single binary bit to be encoded onto the test strip 600, depending on which of the two potential conductive links 602 and 604 are formed on the test strip 600. At least one of the potential conductive links 602/604 is preferably formed on the test strip 600, and both potential conductive links 602/604 may not be formed at the same time without losing the second separate dose sufficiency electrode functionality.

If the potential conductive link 602 is formed on the test strip 600 and the potential conductive link 604 is not formed, then the contact pad 606 becomes the C contact pad (since it is coupled to the counter electrode 322 by the potential conductive link 602). Without the presence of the potential conductive link 604, electrode 326B functions as the actual dose sufficiency counter electrode and contact pad 608 becomes the DC contact pad.

Similarly, if the potential conductive link 604 is formed on the test strip 600 and the potential conductive link 602 is not formed, then the contact pad 608 becomes the C contact pad (since it is coupled to the counter electrode 322 by the potential conductive link 604). Without the presence of the potential conductive link 602, electrode 326A functions as the actual dose sufficiency counter electrode and contact pad 606 becomes the DC contact pad.

Once the test strip 600 is inserted into the test meter, the test meter can easily determine if the potential conductive link 602 is present by checking the conductivity between the CS contact pad and the contact pad 606. Conductivity between these two contact pads indicates the presence of the potential conductive link 602. Similarly, the test meter can determine if the potential conductive link 604 is present by checking the conductivity between the CS contact pad and the contact pad 608. Conductivity between these two contact pads indicates the presence of the potential conductive link 604. Once the test meter has determined which potential conductive link 602/604 is present, it thereafter knows which contact pad to treat as the C contact pad and which to treat as the DC contact pad. In one embodiment, the test meter only checks for the presence or absence of one of the potential conductive links 602/604 and assumes that the other potential conductive link 602/604 is absent or present, respectively. In another embodiment, the test meter confirms the presence or absence of both potential conductive links 602/604, which is a more robust methodology as it is more likely to detect a damaged test strip.

In another embodiment, the code key inserted into the test meter tells the test meter which of the two possible configurations to expect. The test meter then checks to see if the expected contact pad 606/608 is coupled to the CS contact pad. If the expected connection is not present, then the meter checks to see if the other contact pad 606/608 is coupled to the CS contact pad. If the wrong contact pad 606/608 is coupled to the CS contact pad, then the meter indicates a code key error (i.e. a code key has been inserted into the test meter that does not match the test strip inserted into the test meter). If neither contact pad 606/608 is coupled to the CS contact pad, then the test meter indicates a strip error (i.e. the test strip is defective and cannot be used).

More importantly than assigning contact pad functionalities, by determining which potential conductive link 602/604 is present, the test meter has been supplied with one bit of information from the test strip 600. This single bit of information can convey important information to the test meter, such as whether the test strip is designed to test for a first analyte or a second analyte, where the test meter should look for calibration information relating to the test strip, etc. Therefore, supplying a single bit of information by simply reassigning the functions of some of the contact pads on the test strip can easily provide important information to the test meter about the test strip that has been inserted therein.

All publications, prior applications, and other documents cited herein are hereby incorporated by reference in their entirety as if each had been individually incorporated by reference and fully set forth.

While the invention has been illustrated and described in detail in the drawings and foregoing description, the description is to be considered as illustrative and not restrictive in character. Only the preferred embodiment, and certain other embodiments deemed helpful in further explaining how to make or use the preferred embodiment, have been shown. All changes and modifications that come within the spirit of the invention are desired to be protected.

What is claimed is:

1. A method for reading information on a test strip, the method comprising the steps of:
    providing a test strip configured to receive a biological fluid sample and having a substrate with a top surface, a conductive layer formed on at least a portion of the substrate top surface and forming at least one electrode, and at least one information contact pad position defined upon the substrate top surface;
    wherein the presence of the conductive layer in any one of the at least one information contact pad positions conductively connects said any one of the at least one information contact pad positions with the conductive layer to the at least one electrode;
    wherein the absence of the conductive layer in any one of the at least one information contact pad positions disconnects said any one of the at least one information contact pad positions without the conductive layer from the at least one electrode;
    providing a test meter for measuring a concentration of an analyte of interest in the biological fluid sample on the test strip, the test meter having at least one connector contact;
    inserting the test strip into the test meter such that each one of the at least one connector contact separately and distinctly contacts a respective one and only one of the at least one information contact pad position, the test meter detecting the presence or absence of the conductive layer in the at least one information contact pad position; and
    assigning within the test meter a first binary bit to the presence of the conductive layer and a second binary bit to the absence of the conductive layer to read information on the test strip.

2. The method of claim 1, wherein the at least one contact pad position comprises at least seven contact pad positions and the at least one connector contact comprises at least seven connector contacts.

3. The method of claim 1, wherein the at least one contact pad position comprises at least twelve contact pad positions and the at least one connector contact comprises at least twelve connector contacts.

* * * * *